US006410255B1

(12) United States Patent
Pollok et al.

(10) Patent No.: US 6,410,255 B1
(45) Date of Patent: Jun. 25, 2002

(54) OPTICAL PROBES AND ASSAYS

(75) Inventors: Brian A. Pollok, San Diego; Brian D. Hamman; Steven M. Rodems, both of Poway; Lewis R. Makings, Encinitas, all of CA (US)

(73) Assignee: Aurora Biosciences Corporation, San Diego, CA (US)

( * ) Notice: Subject to any disclaimer, the term of this patent is extended or adjusted under 35 U.S.C. 154(b) by 0 days.

(21) Appl. No.: 09/306,542

(22) Filed: May 5, 1999

(51) Int. Cl.[7] .............................. C12Q 1/37; C12Q 1/42

(52) U.S. Cl. ........................................ 435/23; 435/21

(58) Field of Search ....................................... 435/23, 21

(56) References Cited

U.S. PATENT DOCUMENTS

| | | |
|---|---|---|
| 4,314,936 A | 2/1982 | Yaron et al. |
| 5,141,852 A | 8/1992 | Egan et al. |
| 5,221,623 A | 6/1993 | Legocki et al. |
| 5,264,563 A | 11/1993 | Huse |
| 5,491,084 A | 2/1996 | Chalfie |
| 5,527,688 A | 6/1996 | Mallia |
| 5,580,747 A | 12/1996 | Shultz et al. |
| 5,602,021 A | 2/1997 | Davis et al. |
| 5,605,809 A | 2/1997 | Komoriya et al. |
| 5,614,191 A | 3/1997 | Puri et al. |
| 5,625,048 A | 4/1997 | Tsien et al. |
| 5,650,289 A | 7/1997 | Wood |
| 5,674,713 A | 10/1997 | McElroy et al. |
| 5,683,888 A | 11/1997 | Campbell |
| 5,721,133 A | 2/1998 | Dasmahapatra |
| 5,759,787 A | 6/1998 | Strulovici |
| 5,773,237 A | 6/1998 | Wong et al. |
| 5,777,079 A | 7/1998 | Tsien et al. |
| 5,804,387 A | 9/1998 | Cormack et al. |
| 5,804,395 A | 9/1998 | Shade et al. |
| 5,843,746 A | 12/1998 | Tatsumi et al. |

FOREIGN PATENT DOCUMENTS

| | | |
|---|---|---|
| EP | 0 428 000 A1 | 10/1990 |
| EP | 0 639 641 A2 | 8/1994 |
| WO | WO 91/01305 | 2/1991 |
| WO | WO 94/28166 | 12/1994 |
| WO | WO 94/28173 | 12/1994 |
| WO | WO 95/21191 | 8/1995 |
| WO | WO 96/13607 | 5/1996 |
| WO | WO 96/23810 | 8/1996 |
| WO | WO 96/23898 | 8/1996 |
| WO | WO 96/27027 | 9/1996 |
| WO | WO 96/27675 | 9/1996 |
| WO | WO 97/11094 | 3/1997 |
| WO | WO97/28261 | 8/1997 |
| WO | WO97/42320 | 11/1997 |
| WO | WO 98/36099 | 2/1998 |
| WO | WO98/11251 | 3/1998 |
| WO | WO 98/21355 | 5/1998 |
| WO | WO 98/30715 | 7/1998 |
| WO | WO 98/32879 | 7/1998 |

OTHER PUBLICATIONS

Beaudette et al., Journal of Biochemistry vol. 268, No. 28, Oct. 1993 pp. 20825–20830.
Cheng et al, J. Am. Chem. Soc. 1997, 119, 9568–9569.
Clarke, Current Biology, vol. 4, No. 7, 1994.
Cubitt.
Dale et al., FEBS Letters 361 (1995) pp. 191–195.
Erickson et al., The Journal of Biological Chemistry, pp. 19728–19735.
Fujise et al., The Journal of Biological Chemistry, vol. 269, No. 50, Dec. 16, 1994, pp. 31642–31648.
Hanke et al, J. of Bio. Chem., vol. 271, No. 2, Jan. 12, pp. 695–701, (1996).
Hanson et al., Ann. Rev. Biochem. 61:pp. 586–593 (1992).
Hennebicq et al, Glycoconjugate Journal 15:275–282 (1998).
Hurley et al., Science, vol. 249, Aug. 1990, pp. 1012–1016.
Kakinuma et al, J. Bio. Chem., 272:28296–28300 (1997).
Kemp et al., Trends Biochem. Sci. 15–342–346 (1990).
Kemp et al., Methods in Enzymology, vol. 200 1991, pp. 121–156.
Knight, Methods Enzymol. 248:18–34 (1995).
Kolb et al, DDT, 3, 334–342 (1998).
Kwon et al., The Journal of Biological Chemistry, vol. 269 No. 7, pp. 4839–4844.
Levine et al, Analytical Biochemistry 247, 83–88 (1997).
Li et al., Proc. Natl. Acad. Sci. USA vol. 86, pp. 558–562, Jan. 1989.
Linberg et al., TIBS Mar. 1992 pp. 114–119.
Liu et al, Eur. J. Biochem. 167–247–252 (1987).
Loh et al, Molecular and Cellular endocrinology 20:35–44 (1980).

(List continued on next page.)

Primary Examiner—Ponnathapu Achutamurthy
Assistant Examiner—Malgorzata A. Walicka
(74) Attorney, Agent, or Firm—Gray, Cary, Ware & Friedenrich LLP; Lisa A. Haile

(57) ABSTRACT

This invention provides an optical probe useful as an optical probe or sensor of post translational type modifications, such as phosphorylation. The invention comprises a polypeptide moiety, which contains a recognition motif for a post translational type activity and a protease site, which is coupled to a probe moiety. Modification of the polypeptide, by the post translational type activity, results in a modulation of the rate at which a protease cleaves the polypeptide which is sensed by a measurable change in at least one optical property of the optical probe upon cleavage. The present invention also includes a recombinant nucleic acid molecule that encodes an optical probe and a vector and host cell or library of cells that include the recombinant nucleic acid molecule. The optical probe can be used in methods to determine whether a sample, including a cell or a sample from an organism, contains a post-translational type modification activity. Such methods can also be used to determine whether a test chemical modulates the activity of a modifying activity, and thus can be used to identify therapeutic compositions. The identification of such therapeutic compositions can be automated using a system that includes an optical probe.

31 Claims, 8 Drawing Sheets

OTHER PUBLICATIONS

Lu et al., The Journal of Biological Chemistry vol. 269, No. 9, pp.6603–6607 1994.
Lynch et al, Analytical Biochemistry 247, 77–82 (1997).
Ma et al, Biochemistry 31:11772–11777 (1992).
Matayoshi et al., Science 247:954 (1990).
Mitra et al., Gene, 173:13–17 (1996).
Parker et al., DukEngineer Fall 1997.
Patrick et al., DDT vol. 1, No. 8, Aug. 1996, pp. 325–330.
Pearson et al., Methods in Enzymology, vol. 200 pp. 62–81 1991.
Pearson et al., The Journal of Biochemistry vol. 260 No. 27 pp. 14471–14476.
Premont et al., The FASEB Journal Feb. 1995 vol. 9 pp. 175–182.
Rooijen et al, Glycobiology, vol. 9, No. 1:21–30 (1999).
Sala–Newby et al., Biochem J. 1991, 279, 727–732.
Seethala et al, Analytical Biochemistry 253, 210–218 (1997).
Seethala et al, Analytical Biochemistry 255, 257–262 (1998).
Songyang et al., current Biology 4:973–982 (1994).
Songyang et al., Molecular and Cellular Biology Nov. 1996 pp. 6486–6493.
Sterk et al., Journal of Fluorescence, vol. 7, No. 1 1997 (Supplement) pp. 115–s118s.
Stokoe et al., Biochem. J. 296–843–849 (1993).
Stryer, Ann. Rev. Biochem. 47:819–846 (1978).
Tsien et al., Handbook Of Biological Confocal Microscopy 1990 pp. 169–178.
Tsien et al., Trends Cell. Biol. 3:242–245 (1993).
Weber, Fluorescence and Phosphoresence Analysis, Chapter 8: 217–241.
Wilkinson et al., 1994 Elsevier Science Ltd., 53–57.
Wright et al., Proc. Natl. Acad. Sci. USA vol. 78, No. 10, pp. 6048–6050, 1991.
Yaron et al., Analytical Biochem. 95:228–235 (1979).
Yoshida et al, J. of Biol. Chem., vol. 272, No. 27, Jul. 4, 1997, pp. 16884–16888.
Yokoe et al., Nature Biotechnology vol. 14, Oct. 1996, pp. 1252–1256.
Zhang et al., Archives of Biochemistry and Biophysics vol., 315, No. 2 Dec. 1994 pp. 415–424.

SEQUENCE LISTING

```
<160> NUMBER OF SEQ ID NOS: 58

<210> SEQ ID NO 1
<211> LENGTH: 9
<212> TYPE: PRT
<213> ORGANISM: Artificial sequence
<220> FEATURE:
<223> OTHER INFORMATION: Optical probe specific motif

<400> SEQUENCE: 1
```

Met Glu Glu Ile Tyr Gly Ile Leu Ser
1               5

<210> SEQ ID NO 2
<211> LENGTH: 9
<212> TYPE: PRT
<213> ORGANISM: Artificial sequence
<220> FEATURE:
<223> OTHER INFORMATION: Optical probe specific motif

<400> SEQUENCE: 2

Asp Glu Glu Ile Tyr Glu Ser Leu Glu
1               5

<210> SEQ ID NO 3
<211> LENGTH: 11
<212> TYPE: PRT
<213> ORGANISM: Artificial sequence
<220> FEATURE:
<223> OTHER INFORMATION: Optical probe specific motif

<400> SEQUENCE: 3

Gly Glu Glu Glu Ile Tyr Gly Glu Ile Glu Lys
1               5                   10

<210> SEQ ID NO 4
<211> LENGTH: 9
<212> TYPE: PRT
<213> ORGANISM: Artificial sequence
<220> FEATURE:
<223> OTHER INFORMATION: Optical probe specific motif

<400> SEQUENCE: 4

Ala Glu Ala Ile Tyr Ala Ala Pro Leu
1               5

<210> SEQ ID NO 5
<211> LENGTH: 8
<212> TYPE: PRT
<213> ORGANISM: Artificial sequence
<220> FEATURE:
<223> OTHER INFORMATION: Optical probe specific motif

<400> SEQUENCE: 5

Glu Pro Ile Tyr Met Leu Ser Leu
1               5

<210> SEQ ID NO 6
<211> LENGTH: 8
<212> TYPE: PRT
<213> ORGANISM: Artificial sequence
<220> FEATURE:
<223> OTHER INFORMATION: Optical probe specific motif

<400> SEQUENCE: 6

Glu Glu Glu Tyr Met Met Met Met
1               5

<210> SEQ ID NO 7
<211> LENGTH: 9
<212> TYPE: PRT
<213> ORGANISM: Artificial sequence
<220> FEATURE:
<223> OTHER INFORMATION: Optical probe specific motif
<221> NAME/KEY: VARIANT
<222> LOCATION: (1)..(9)
<223> OTHER INFORMATION: Xaa is any amino acid

```
<400> SEQUENCE: 7

Glu Glu Glu Glu Tyr Val Val Ile Xaa
1               5

<210> SEQ ID NO 8
<211> LENGTH: 9
<212> TYPE: PRT
<213> ORGANISM: Artificial sequence
<220> FEATURE:
<223> OTHER INFORMATION: Optical probe specific motif

<400> SEQUENCE: 8

Glu Glu Glu Glu Tyr Val Leu Leu Val
1               5

<210> SEQ ID NO 9
<211> LENGTH: 9
<212> TYPE: PRT
<213> ORGANISM: Artificial sequence
<220> FEATURE:
<223> OTHER INFORMATION: Optical probe specific motif

<400> SEQUENCE: 9

Ala Glu Glu Glu Tyr Phe Val Leu Met
1               5

<210> SEQ ID NO 10
<211> LENGTH: 9
<212> TYPE: PRT
<213> ORGANISM: Artificial sequence
<220> FEATURE:
<223> OTHER INFORMATION: Optical probe with p-Ser in P'(sub 1)

<400> SEQUENCE: 10

Arg Arg Arg Phe Ser Ile Ile Ile Ile
1               5

<210> SEQ ID NO 11
<211> LENGTH: 9
<212> TYPE: PRT
<213> ORGANISM: Artificial sequence
<220> FEATURE:
<223> OTHER INFORMATION: Optical probe with p-Ser P'(sub 2)

<400> SEQUENCE: 11

Arg Arg Phe Arg Ser Ile Ile Ile Ile
1               5

<210> SEQ ID NO 12
<211> LENGTH: 11
<212> TYPE: PRT
<213> ORGANISM: Artificial sequence
<220> FEATURE:
<223> OTHER INFORMATION: Optical probe with p-Ser in P'(sub 1)

<400> SEQUENCE: 12

Arg Arg Arg Lys Phe Ser Leu Arg Arg Lys Ala
1               5                   10

<210> SEQ ID NO 13
<211> LENGTH: 10
<212> TYPE: PRT
<213> ORGANISM: Artificial sequence
<220> FEATURE:
<223> OTHER INFORMATION: Optical probe with p-Ser in P'(sub 1)
```

```
<400> SEQUENCE: 13

Leu Arg Arg Arg Phe Ser Ala Ser Asn Leu
1               5                   10

<210> SEQ ID NO 14
<211> LENGTH: 9
<212> TYPE: PRT
<213> ORGANISM: Artificial sequence
<220> FEATURE:
<223> OTHER INFORMATION: Optical probe with p-Ser in P'(sub 1)

<400> SEQUENCE: 14

Lys Arg Gln Phe Ser Ile Asp Leu Lys
1               5

<210> SEQ ID NO 15
<211> LENGTH: 9
<212> TYPE: PRT
<213> ORGANISM: Artificial sequence
<220> FEATURE:
<223> OTHER INFORMATION: Optical probe with p-Ser P'(sub 2)

<400> SEQUENCE: 15

Lys Arg Phe Gln Ser Ile Asp Leu Lys
1               5

<210> SEQ ID NO 16
<211> LENGTH: 11
<212> TYPE: PRT
<213> ORGANISM: Artificial sequence
<220> FEATURE:
<223> OTHER INFORMATION: Optical probe with p-Ser in P'(sub 1)

<400> SEQUENCE: 16

Gly Asp Gln Asp Thr Tyr Ser Leu Leu Asp Lys
1               5                   10

<210> SEQ ID NO 17
<211> LENGTH: 10
<212> TYPE: PRT
<213> ORGANISM: Artificial sequence
<220> FEATURE:
<223> OTHER INFORMATION: Optical probe with p-Ser P'(sub 2)

<400> SEQUENCE: 17

Gly Asp Gln Asp Tyr Leu Ser Leu Asp Lys
1               5                   10

<210> SEQ ID NO 18
<211> LENGTH: 9
<212> TYPE: PRT
<213> ORGANISM: Artificial sequence
<220> FEATURE:
<223> OTHER INFORMATION: Optical probe with p-Ser in P'(sub 1)

<400> SEQUENCE: 18

Glu Asp Glu Phe Ser Glu Asp Glu Glu
1               5

<210> SEQ ID NO 19
<211> LENGTH: 9
<212> TYPE: PRT
<213> ORGANISM: Artificial sequence
<220> FEATURE:
<223> OTHER INFORMATION: Optical probe with p-Ser P'(sub 2)

<400> SEQUENCE: 19
```

Glu Asp Phe Glu Ser Glu Asp Glu Glu
1               5

<210> SEQ ID NO 20
<211> LENGTH: 9
<212> TYPE: PRT
<213> ORGANISM: Artificial sequence
<220> FEATURE:
<223> OTHER INFORMATION: Optical probe with p-Ser in P'(sub 1)

<400> SEQUENCE: 20

His His His Phe Ser Pro Arg Lys Arg
1               5

<210> SEQ ID NO 21
<211> LENGTH: 9
<212> TYPE: PRT
<213> ORGANISM: Artificial sequence
<220> FEATURE:
<223> OTHER INFORMATION: Optical probe with p-Ser P'(sub 2)

<400> SEQUENCE: 21

His His Phe Arg Ser Pro Arg Lys Arg
1               5

<210> SEQ ID NO 22
<211> LENGTH: 9
<212> TYPE: PRT
<213> ORGANISM: Artificial sequence
<220> FEATURE:
<223> OTHER INFORMATION: Optical probe with p-Ser in P'(sub 1)

<400> SEQUENCE: 22

His His His Phe Ser Pro Arg Arg Arg
1               5

<210> SEQ ID NO 23
<211> LENGTH: 9
<212> TYPE: PRT
<213> ORGANISM: Artificial sequence
<220> FEATURE:
<223> OTHER INFORMATION: Optical probe with p-Ser P'(sub 2)

<400> SEQUENCE: 23

His His Phe Lys Ser Pro Arg Arg Arg
1               5

<210> SEQ ID NO 24
<211> LENGTH: 11
<212> TYPE: PRT
<213> ORGANISM: Artificial sequence
<220> FEATURE:
<223> OTHER INFORMATION: Optical probe with p-Ser in P'(sub 1)

<400> SEQUENCE: 24

Arg Val Asp Glu Pro Phe Ser Pro Gly Glu Lys
1               5                   10

<210> SEQ ID NO 25
<211> LENGTH: 8
<212> TYPE: PRT
<213> ORGANISM: Artificial sequence
<220> FEATURE:
<223> OTHER INFORMATION: Optical probe with p-Ser in P'(sub 1)

<400> SEQUENCE: 25

```
Pro Arg Pro Phe Ser Val Pro Pro
1               5

<210> SEQ ID NO 26
<211> LENGTH: 9
<212> TYPE: PRT
<213> ORGANISM: Artificial sequence
<220> FEATURE:
<223> OTHER INFORMATION: Optical probe with p-Ser in P'(sub 1)

<400> SEQUENCE: 26

Arg Arg Arg Phe Ser Leu Arg Arg Ile
1               5

<210> SEQ ID NO 27
<211> LENGTH: 9
<212> TYPE: PRT
<213> ORGANISM: Artificial sequence
<220> FEATURE:
<223> OTHER INFORMATION: Optical probe with p-Ser P'(sub 2)

<400> SEQUENCE: 27

Arg Arg Phe Gly Ser Leu Arg Arg Ile
1               5

<210> SEQ ID NO 28
<211> LENGTH: 9
<212> TYPE: PRT
<213> ORGANISM: Artificial sequence
<220> FEATURE:
<223> OTHER INFORMATION: Optical probe with p-Ser in P'(sub 1)

<400> SEQUENCE: 28

Arg Arg Arg Phe Ser Arg Arg Arg Arg
1               5

<210> SEQ ID NO 29
<211> LENGTH: 9
<212> TYPE: PRT
<213> ORGANISM: Artificial sequence
<220> FEATURE:
<223> OTHER INFORMATION: Optical probe with p-Ser P'(sub 2)

<400> SEQUENCE: 29

Arg Arg Phe His Ser Arg Arg Arg Arg
1               5

<210> SEQ ID NO 30
<211> LENGTH: 9
<212> TYPE: PRT
<213> ORGANISM: Artificial sequence
<220> FEATURE:
<223> OTHER INFORMATION: Optimal recognition motif for the kinase

<400> SEQUENCE: 30

Met Glu Glu Ile Tyr Gly Ile Phe Phe
1               5

<210> SEQ ID NO 31
<211> LENGTH: 9
<212> TYPE: PRT
<213> ORGANISM: Artificial sequence
<220> FEATURE:
<223> OTHER INFORMATION: Optimal recognition motif for the kinase

<400> SEQUENCE: 31

Asp Glu Glu Ile Tyr Glu Glu Leu Glu
```

<210> SEQ ID NO 32
<211> LENGTH: 11
<212> TYPE: PRT
<213> ORGANISM: Artificial sequence
<220> FEATURE:
<223> OTHER INFORMATION: Optimal recognition motif for the kinase

<400> SEQUENCE: 32

Gly Glu Glu Glu Ile Tyr Gly Glu Phe Glu Lys
1               5                   10

<210> SEQ ID NO 33
<211> LENGTH: 9
<212> TYPE: PRT
<213> ORGANISM: Artificial sequence
<220> FEATURE:
<223> OTHER INFORMATION: Optimal recognition motif for the kinase
<221> NAME/KEY: VARIANT
<222> LOCATION: (1)..(9)
<223> OTHER INFORMATION: Xaa is any amino acid

<400> SEQUENCE: 33

Ala Xaa Val Ile Tyr Ala Ala Pro Phe
1               5

<210> SEQ ID NO 34
<211> LENGTH: 9
<212> TYPE: PRT
<213> ORGANISM: Artificial sequence
<220> FEATURE:
<223> OTHER INFORMATION: Optimal recognition motif for the kinase
<221> NAME/KEY: VARIANT
<222> LOCATION: (1)..(9)
<223> OTHER INFORMATION: Xaa is any amino acid

<400> SEQUENCE: 34

Xaa Glu Pro Ile Tyr Met Phe Phe Phe
1               5

<210> SEQ ID NO 35
<211> LENGTH: 9
<212> TYPE: PRT
<213> ORGANISM: Artificial sequence
<220> FEATURE:
<223> OTHER INFORMATION: Optimal recognition motif for the kinase
<221> NAME/KEY: VARIANT
<222> LOCATION: (1)..(9)
<223> OTHER INFORMATION: Xaa is any amino acid

<400> SEQUENCE: 35

Xaa Glu Glu Glu Tyr Met Met Met Phe
1               5

<210> SEQ ID NO 36
<211> LENGTH: 9
<212> TYPE: PRT
<213> ORGANISM: Artificial sequence
<220> FEATURE:
<223> OTHER INFORMATION: Optimal recognition motif for the kinase
<221> NAME/KEY: VARIANT
<222> LOCATION: (1)..(9)
<223> OTHER INFORMATION: Xaa is any amino acid

<400> SEQUENCE: 36

Glu Glu Glu Glu Tyr Val Phe Ile Xaa
1               5

```
<210> SEQ ID NO 37
<211> LENGTH: 9
<212> TYPE: PRT
<213> ORGANISM: Artificial sequence
<220> FEATURE:
<223> OTHER INFORMATION: Optimal recognition motif for the kinase

<400> SEQUENCE: 37

Glu Glu Glu Glu Tyr Phe Glu Leu Val
1               5

<210> SEQ ID NO 38
<211> LENGTH: 9
<212> TYPE: PRT
<213> ORGANISM: Artificial sequence
<220> FEATURE:
<223> OTHER INFORMATION: Optimal recognition motif for the kinase

<400> SEQUENCE: 38

Ala Glu Glu Glu Tyr Phe Phe Leu Phe
1               5

<210> SEQ ID NO 39
<211> LENGTH: 9
<212> TYPE: PRT
<213> ORGANISM: Artificial sequence
<220> FEATURE:
<223> OTHER INFORMATION: Optimal probe motif

<400> SEQUENCE: 39

Arg Arg Arg Arg Ser Ile Ile Phe Ile
1               5

<210> SEQ ID NO 40
<211> LENGTH: 10
<212> TYPE: PRT
<213> ORGANISM: Artificial sequence
<220> FEATURE:
<223> OTHER INFORMATION: Optimal probe motif

<400> SEQUENCE: 40

Arg Arg Arg Lys Phe Ser Phe Arg Arg Lys
1               5                   10

<210> SEQ ID NO 41
<211> LENGTH: 10
<212> TYPE: PRT
<213> ORGANISM: Artificial sequence
<220> FEATURE:
<223> OTHER INFORMATION: Optimal probe motif

<400> SEQUENCE: 41

Leu Arg Arg Arg Leu Ser Asp Ser Asn Leu
1               5                   10

<210> SEQ ID NO 42
<211> LENGTH: 9
<212> TYPE: PRT
<213> ORGANISM: Artificial sequence
<220> FEATURE:
<223> OTHER INFORMATION: Optimal probe motif

<400> SEQUENCE: 42

Lys Arg Gln Gln Ser Phe Asp Leu Phe
1               5
```

```
<210> SEQ ID NO 43
<211> LENGTH: 10
<212> TYPE: PRT
<213> ORGANISM: Artificial sequence
<220> FEATURE:
<223> OTHER INFORMATION: Optimal probe motif

<400> SEQUENCE: 43

Phe Asp Thr Gly Ser Ile Ile Ile Phe Phe
1               5                   10

<210> SEQ ID NO 44
<211> LENGTH: 9
<212> TYPE: PRT
<213> ORGANISM: Artificial sequence
<220> FEATURE:
<223> OTHER INFORMATION: Optimal probe motif

<400> SEQUENCE: 44

Glu Asp Glu Glu Ser Glu Asp Glu Glu
1               5

<210> SEQ ID NO 45
<211> LENGTH: 9
<212> TYPE: PRT
<213> ORGANISM: Artificial sequence
<220> FEATURE:
<223> OTHER INFORMATION: Optimal probe motif

<400> SEQUENCE: 45

His His His Arg Ser Pro Arg Lys Arg
1               5

<210> SEQ ID NO 46
<211> LENGTH: 9
<212> TYPE: PRT
<213> ORGANISM: Artificial sequence
<220> FEATURE:
<223> OTHER INFORMATION: Optimal probe motif

<400> SEQUENCE: 46

His His His Lys Ser Pro Arg Arg Arg
1               5

<210> SEQ ID NO 47
<211> LENGTH: 11
<212> TYPE: PRT
<213> ORGANISM: Artificial sequence
<220> FEATURE:
<223> OTHER INFORMATION: Optimal probe motif

<400> SEQUENCE: 47

Arg Val Asp Glu Pro Asp Ser Pro Gly Glu Lys
1               5                   10

<210> SEQ ID NO 48
<211> LENGTH: 8
<212> TYPE: PRT
<213> ORGANISM: Artificial sequence
<220> FEATURE:
<223> OTHER INFORMATION: Optimal probe motif

<400> SEQUENCE: 48

Pro Arg Pro Ala Ser Val Pro Pro
1               5

<210> SEQ ID NO 49
```

```
<211> LENGTH: 9
<212> TYPE: PRT
<213> ORGANISM: Artificial sequence
<220> FEATURE:
<223> OTHER INFORMATION: Optimal probe motif

<400> SEQUENCE: 49

Arg Arg Phe Gly Ser Leu Arg Arg Phe
1               5

<210> SEQ ID NO 50
<211> LENGTH: 9
<212> TYPE: PRT
<213> ORGANISM: Artificial sequence
<220> FEATURE:
<223> OTHER INFORMATION: Optimal probe motif

<400> SEQUENCE: 50

Arg Arg Arg His Ser Arg Arg Arg Arg
1               5

<210> SEQ ID NO 51
<211> LENGTH: 4
<212> TYPE: PRT
<213> ORGANISM: Artificial sequence
<220> FEATURE:
<223> OTHER INFORMATION: Enzyme recognition motif
<221> NAME/KEY: VARIANT
<222> LOCATION: (1)..(4)
<223> OTHER INFORMATION: Xaa is any amino acid

<400> SEQUENCE: 51

Cys Ala Ala Xaa
1

<210> SEQ ID NO 52
<211> LENGTH: 4
<212> TYPE: PRT
<213> ORGANISM: Artificial sequence
<220> FEATURE:
<223> OTHER INFORMATION: Enzyme recognition motif

<400> SEQUENCE: 52

Cys Ala Ala Leu
1

<210> SEQ ID NO 53
<211> LENGTH: 5
<212> TYPE: PRT
<213> ORGANISM: Artificial sequence
<220> FEATURE:
<223> OTHER INFORMATION: Glycosylation activity consensus sequence motif
<221> NAME/KEY: VARIANT
<222> LOCATION: (1)..(5)
<223> OTHER INFORMATION: Xaa residue 1 is any uncharged amino acid and
      Xaa at residue 4 is any small amino acid

<400> SEQUENCE: 53

Xaa Thr Pro Xaa Pro
1               5

<210> SEQ ID NO 54
<211> LENGTH: 5
<212> TYPE: PRT
<213> ORGANISM: Artificial sequence
<220> FEATURE:
<223> OTHER INFORMATION: Substrate preference motif

<400> SEQUENCE: 54
```

```
Glu Glu Glu Tyr Phe
1               5

<210> SEQ ID NO 55
<211> LENGTH: 5
<212> TYPE: PRT
<213> ORGANISM: Artificial sequence
<220> FEATURE:
<223> OTHER INFORMATION: Substrate preference motif

<400> SEQUENCE: 55

Glu Glu Glu Tyr Val
1               5

<210> SEQ ID NO 56
<211> LENGTH: 5
<212> TYPE: PRT
<213> ORGANISM: Artificial sequence
<220> FEATURE:
<223> OTHER INFORMATION: Substrate preference motif
<221> NAME/KEY: VARIANT
<222> LOCATION: (1)..(5)
<223> OTHER INFORMATION: Xaa is any amino acid

<400> SEQUENCE: 56

Glu Xaa Tyr Xaa Phe
1               5

<210> SEQ ID NO 57
<211> LENGTH: 4
<212> TYPE: PRT
<213> ORGANISM: Artificial sequence
<220> FEATURE:
<223> OTHER INFORMATION: Substrate preference motif

<400> SEQUENCE: 57

Tyr Met Met Met
1

<210> SEQ ID NO 58
<211> LENGTH: 5
<212> TYPE: PRT
<213> ORGANISM: Artificial sequence
<220> FEATURE:
<223> OTHER INFORMATION: Caspase 3 cleavege site: peptide between
      residue 4 and 5
<221> NAME/KEY: VARIANT
<222> LOCATION: (1)..(5)
<223> OTHER INFORMATION: Xaa at residues 2 and 4 are any amino acid,
      Xaa at residue 5 is Asp or preferred any neutral amino acid

<400> SEQUENCE: 58

Asp Xaa Xaa Asp Xaa
1               5
```

OPTICAL PROBES AND ASSAYS

FIELD OF THE INVENTION

The present invention relates generally to the fields of chemistry and biology. More particularly, the present invention relates to optical probes for post translational type modification activities, such as phosphorylation, and methods for their use.

INTRODUCTION

Systems and methods for rapidly identifying chemicals with biological activity in samples, especially small liquid samples, is of particular relevance to the agrochemical and pharmaceutical fields. Various strategies are typically used to reduce processing times and associated costs of screening large numbers of chemical entities, including simplified assay design, automation, robotics and miniaturization of sample size. The advent of high throughput analysis and increasing use of miniaturized formats has led to the development of high density plate formats. For example, containing 384, 864 and 3456 wells as described in U.S. patent application Ser. No. 08/868,049 Entitled "Low Background Multi-Well Plates with greater than 864 Wells for Fluorescence Measurements of Biological and Biochemical Samples," filed Jul. 3, 1997, now pending. Even higher density sample processing systems, for example using chips that contain miniaturized microfluidic devices are being developed (see, for example, R & D Magazine, November 1998, pages 38 to 43 entitled "Lab-on-a Chip: Biotech's next California Gold Rush").

Higher density plates enable faster analysis and handling of large sample or chemical libraries, such as in automated screening systems, but place considerable constraints on the assays that can be successfully employed within them. In particular, there is a need to develop assays that are compatible with miniaturized systems and which give accurate and reproducible assay results. Central to this need is a requirement for high sensitivity assays based on optical analysis, such as fluorescence or luminescence that do not require wash steps (e.g. "addition only assays").

One of the largest and most important classes of intracellular activities for which drugs may be particularly valuable are those involved in post-translational modification activities. These activities are typically directed to the modification of proteins and nucleic acids within living cells to effect changes in the biological activity and function of these molecules. The major methods of protein or polypeptide, post-translational modification include protein phosphorylation, methylation, prenylation, glycosylation, ubiquitination sulfation and proteolysis (see generally Cells. A Laboratory Manual, Cold Spring Harbor Laboratory Press (1998) review). Major methods of nucleic acid modification include methylation, ADP-ribsoylation and restriction digestion. A variety of environmental stimuli such as the presence of growth factors, hormones, changes in the cell cycle and toxins can transiently modulate the post-translational state of many intracellular components. The rapid development of specific, and effective inhibitors for a particular post-translational activity requires the development of suitable assays that can reliably and -sensitively detect these activities in a high throughput screening system.

In spite of their great potential importance however, there are few existing methods of measuring such activities that are homogenous, non radioactive and sensitive enough to accurately and reproducible work in high throughput, or ultra high throughput screening systems. Such assays, by reducing the time required to identify and develop useful chemicals, can dramatically increase the value of a new drug by enabling its patentability and increasing it's period of exclusivity in the market.

Examples of such post-translational activities include, amongst others, protein methylation and prenylation. Protein prenylation involves the addition of isoprenoid moieties such as farnesyl and geranylgeranyl to proteins, and is a major mechanism of post-translational modification for many membrane-associated proteins. (Clark, 1992 *Protein isoprenylation and methylation at carboxyl-terminal cysteine residues.* Annu. Rev. Biochem. 61 355–386). In most cases, the amino acid derivatized with the isoprenoid is a cysteine, or cysteines close to the carboxyl-terminus of the protein. Present methods of measuring protein prenylation and methylation typically involve labeling cells with radioactive precursors such as $[^3H]$-mevalonate or $[^3H]$-S-adenosylmethionine, isolation of the protein of interest and measurement of radioactive incorporation. There is thus a need for assays for these activities that are sensitive, simple to use, non-radioactive and adaptable to high throughput screening methods.

Another important example of post-translational modification is protein glycosylation, which plays an extremely important role in the function of a significant number of proteins (Varki, 1993, *Biological roles of oligosaccharides.* Glycobiology 3 97–130). Protein glycosylation, unlike most other types of post-translational modification provides a wide diversity in the oligosaccharides added to a protein because of the potential for branching after the addition of the first sugar residue. Present methods of measuring glycosylation typically involve determining radioactive incorporation of a precursor oligosaccharide into a protein, isolating the protein and then measuring specific radioactive incorporation into a protein. There is thus a need for fluorescence or luminescence based assays for these activities that are adaptable to high throughput screening methods. It is one objective of the present invention to provide optical probes and methods of use that meet this need.

Protein kinases and phosphatases are generally recognized as one of the more important general mechanisms of regulating protein function. A recent review and analysis of diseases associated with genetic defects in protein kinases lists over 400 specific disease states associated with these activities alone. Protein kinases act on proteins via the addition of phosphate groups (phosphorylation) primarily on the amino acids, tyrosine, serine or threonine. Protein phosphatases in contrast, act to remove these phosphate groups thereby reversing the effects of phosphorylation. Changes in the phosphorylation state of proteins, can regulate the enzymatic activity, protein localization and protein-protein interactions of a particular protein within a cell. Such changes can subsequently modulate virtually every aspect of cellular metabolism, regulation, growth and differentiation. The overall balance of kinase and phosphatase activities in a cell is a primary determinant of the phosphorylation state of a protein at any one time.

However, current methods of measuring protein kinases, have many disadvantages, which prevents or hampers the ability to rapidly screen for drugs using miniaturized automated formats of many thousands of compounds.

For example, many current methods of measuring their activity rely on the incorporation and measurement of $^{32}P$ into the protein substrates of interest. In whole cells, this necessitates the use of high levels of radioactivity to efficiently label the cellular ATP pool and to ensure that the target protein is efficiently labeled with radioactivity. After incubation with test drugs, the cells must be lysed and the protein of interest purified to determine its relative degree of phosphorylation. This method requires large numbers of cells, long preincubation times, careful manipulation, and washing steps to avoid artifactual phosphorylation or dephosphorylation. Furthermore, this kinase assay approach requires purification of the target protein, and final radioactive incorporation into target proteins is usually very low giving the assay poor sensitivity. In high throughput screening operations, this approach requires large amounts of radioactivity, which can be an environmental and health hazard.

Alternative kinase assay methods, such as those based on phosphorylation-specific antibodies using ELISA-type approaches, involve the difficulty of producing antibodies that distinguish between phosphorylated and non-phosphorylated proteins.

Furthermore, most kinase measurements have the requirement for cell lysis, multiple incubations, and washing stages that are time consuming, complex to automate, and potentially susceptible to artifacts.

There is thus a need for assays for enzymes, such as those involved in post-translational modification, that are sensitive, simple to use, applicable to virtually any activity and adaptable to high throughput screening methods. Preferably, such assays would not utilize radioactive materials so that the assays would be safe and not generate hazardous wastes. The present invention addresses these needs, and provides additional benefits as well.

SUMMARY OF THE INVENTION

This invention provides a fluorescent or bioluminescent substrate useful as an optical probe or sensor of post translational type modifications, such as phosphorylation. In one embodiment, the invention comprises a polypeptide moiety, which contains a recognition motif for a post translational type activity and a protease site, which is coupled to a probe moiety. Typically, the presence of a modification at the recognition motif alters protease activity at the protease site resulting in a modulation of the cleavage rate of the protease. Cleavage is sensed by a measurable change in at least one optical property of the optical probe upon cleavage at the protease site, FIG. 1.

In one embodiment the probe is a fluorescent or luminescent moiety.

In another embodiment, the invention further comprises a fluorescent quencher coupled to the polypeptide that quenches emission from the first probe moiety. In this embodiment, the first probe moiety and the quencher moiety are coupled to the polypeptide such that the recognition motif and the protease site are located between them (FIG. 1). In this case, cleavage of the polypeptide by a protease results in an alteration in the fluorescence emission of the first probe moiety that may be used to determine post-translational activity.

In another embodiment, the optical probe may further comprise a second probe moiety coupled to the polypeptide that participates in energy transfer with the first probe moiety. In this embodiment, the first probe moiety and the second probe moiety are coupled to the polypeptide such that recognition motif and the protease site are located between them. In this case, cleavage of the polypeptide by a protease results in an alteration in energy transfer between the first probe moiety and the second probe moiety that may be used to determine post-translational activity.

The invention also provides methods for using the optical probes of the invention to determine whether a sample contains a post-translational type modification activity such as protein phosphorylation or dephosphorylation, methylation, prenylation or glycosylation. The method consisting of; i), contacting the optical probe with a sample, usually containing or suspected of containing a post translational type activity; ii), contacting the sample and optical probe with a protease, and iii), determining at least one optical property of said optical probe, or product thereof.

In another embodiment, the invention provides methods for using the optical probes of the invention to determine whether a test chemical modulates the activity of a post-translational type activity.

In another aspect, the invention provides a library of optical probes, each with a unique peptide sequence for use in selecting an optimal sequence specificity of a post-translational type activity.

Another aspect of the present invention includes a compound or therapeutic identified by at least one method of the present invention. These methods can include monitoring the efficacy and/or toxicology of said therapeutic in an in vitro or in vivo model. The compound can be provided in therapeutically acceptable carrier and can form a therapeutic composition.

A further aspect of the present invention includes various systems for spectroscopic measurements. In one embodiment, the system typically includes at least one reagent for an assay and a device, said device comprising a container and a platform. The container can include the optical sensor compounds of the present invention, and additional reagents necessary for the post-translational type activity. Addition of a sample to the container, followed by the addition of a protease after a given time results in a change in at least one fluorescent property of the optical probes of the present invention that can be used to determine the post-translational type activity of the sample.

In another embodiment the system can include a microfluidic spectroscopic system comprising at least one fluid containing structure with at least one electro-osmotic or electrophoretic system to control fluid movement within that structure.

BRIEF DESCRIPTION OF THE DRAWINGS

The accompanying drawings, which are incorporated in and form part of the specification, merely illustrate embodiments of the present invention. Together with the remainder of the specification, they are meant to serve to explain certain principles of the invention to those of skill in the art.

In FIG. 1, a first probe moiety, 1, is attached to a polypeptide, 5, that comprises a post-translational modification recognition site for an activity, 6 (shown hatched in FIG. 1) and a protease site for a protease, 7, (shown filled in FIG. 1). In one embodiment of the present invention, the optical probe may be attached to a solid surface, 4, such as a bead. In another embodiment, the optical probe may further comprise a quencher, 2, that is separated from the first probe moiety, 1, by the polypeptide, 5. In another embodiment, the optical probe may comprise a second probe moiety, 3, that is again separated from the first probe moiety 1, by the polypeptide, 5.

DETAILED DESCRIPTION OF THE INVENTION

Figure 1:
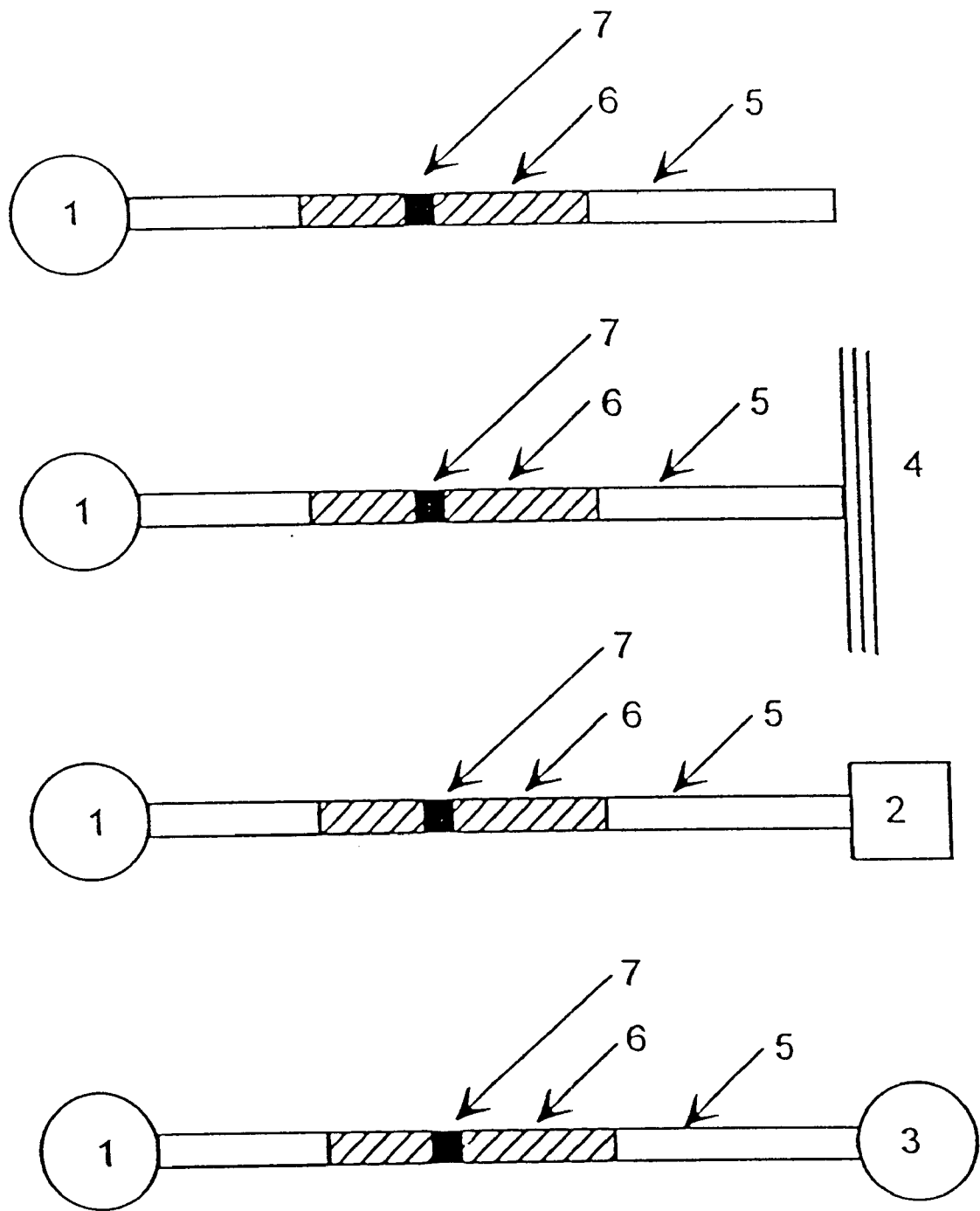
FIG. 1 Shows a schematic representation of some different embodiments of the present invention.

The present invention recognizes that optical probes can be designed to act as optical sensors of post-translational activities through the creation of engineered molecules. In the present invention, post-translational modification of a polypeptide results in the modulation of the rate and efficiency of cleavage of the modified polypeptide compared to the non-modified peptide. The attachment of at least one probe moiety to the peptide couples the cleavage of the optical probe to a change in a fluorescence property of the substrate that may be used to determine the amount of post-translational activity in a sample, FIG. 1.

Abbreviations t-Boc, tert-butyloxycarbonyl; Bzl, benzyl; CaMK, calmodulin dependent kinase; CKI, casein kinase 1; PDGF, platelet derived growth factor; Fmoc, fluorenylmethyloxycarbonyl; EGF, epidermal growth factor; ELISA, enzyme-linked immuno absorbant assay; FGF, fibroblast growth factor; HF, hydrogen fluoride; HOBT, N-Hydroxybenzotriazole; PyBop, Benzotriazole-MBHA, methylbenzhydrylamine; DCM, dichloromethane; DIEA, diisopropylethylamine; GABA, □ amino-n-butyric acid; FITC, fluorescein isothiocyanate; TFA, trifluoroacetic acid; DMF, dimethyl-formamide cl-yl-oxy-tris-pyyrolidino-phosphonium hexafluorophosphate; TFA, trifluoroacteic acid.

Definitions

Generally, the nomenclature used herein and many of the fluorescence, computer, detection, chemistry and laboratory procedures described below are those well known and commonly employed in the art. Standard techniques are usually used for chemical synthesis, fluorescence, optics, molecular biology, computer software and integration. Generally, chemical reactions, cell assays and enzymatic reactions are performed according to the manufacturer's specifications where appropriate. The techniques and procedures are generally performed according to conventional methods in the art and various general references. (Lakowicz, J. R. *Topics in Fluorescence Spectroscopy*, (3 volumes) New York: Plenum Press (1991), and Lakowicz, J. R. Emerging applications of fluorescence spectroscopy to cellular imaging: lifetime imaging, metal-ligand probes, multi-photon excitation and light quenching. Scanning Microsc Suppl Vol. 10 (1996) pages 213–24, for fluorescence techniques; Sambrook et al. *Molecular Cloning: A Laboratory Manual*, $2^{nd}$ ed. (1989) Cold Spring Harbor Laboratory Press, Cold Spring Harbor, N.Y., for molecular biology methods; Cells: A Laboratory Manual, $1^{st}$ edition (1998) Cold Spring Harbor Laboratory Press, Cold Spring Harbor, N.Y., for cell biology methods; Optics Guide 5 Melles Griot® Irvine Calif., and *Optical Waveguide Theory*, Snyder & Love published by Chapman & Hall for general optical methods, which are incorporated herein by reference which are provided throughout this document).

As employed throughout the disclosure, the following terms, unless otherwise indicated, shall be understood to have the following meanings:

The term "acceptor" refers to a quencher that operates via energy transfer. Acceptors may re-emit the transferred energy as fluorescence and are "acceptor fluorescent moieties". Examples of acceptors include coumarins and related fluorophores, xanthenes such as fluoresceins, fluorescent proteins rhodols, and rhodamines, resorufins, cyanines, difluoroboradiazaindacenes, and phthalocyanines. Other chemical classes of acceptors generally do not re-emit the transferred energy. Examples include indigos, benzoquinones, anthraquinones, azo compounds, nitro compounds, indoanilines, and di- and triphenylmethanes.

The term "bead" refers to a substantially spherical particle such as a sphere or microsphere. Beads may be used within a wide size range. Preferred beads are typically within the range of 0.01 to 100 μm in diameter. Beads may be composed of any material and may be substantially inert or comprise fluorescent, luminescence, electro-luminescent, chemo-luminescent, magnetic or paramagnetic probes. Such beads are commercially available from a variety of sources including Molecular Probes, Sigma or Polysciences.

The terms "cleavage site" or "protease site" refers to the bond cleaved by the protease (e.g. a scissile bond) and typically the surrounding three amino acids of either side of the bond. The letters "$P_1$", "$P_2$", "$P_3$" etc, refer to the amino acid positions, 1 amino acid, 2 amino acids and 3 amino acids N-terminal to the scissile bond. The letters "$P'_1$", "$P'_2$", "$P'_3$", refer to the amino acids positions 1 amino acid, 2 amino acids and 3 amino acids C-terminal to the scissile bond, as shown below;

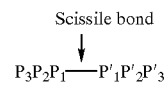

Scissile bond $P_3P_2P_1$——$P'_1P'_2P'_3$

The term "engineered recognition motif" refers to a recognition motif that has been modified from the naturally existing sequence by at least one amino acid substitution.

The term "engineered protease site" refers to a protease site that has been modified from the naturally existing sequence by at least one amino acid substitution.

The term "fluorescent moiety" refers to a moiety that can absorb electromagnetic energy and is capable of at least partially remitting some fraction of that energy as electromagnetic radiation over some time period. Suitable fluorescent moieties include, but are not limited to, coumarins and related dyes, xanthene dyes such as fluoresceins, rhodols, and rhodamines, resorufins, cyanine dyes, bimanes, acridines, isoindoles, dansyl dyes, aminophthalic hydrazides such as luminol, and isoluminol derivatives, aminophthalimides, aminonaphthalimides, aminobenzofurans, aminoquinolines, dicyanohydroquinones, semiconductor fluorescent nanocrystals, fluorescent proteins and fluorescent europium and terbium complexes and related compounds.

The term "fluorescent property" refers to any one of the following, the molar extinction coefficient at an appropriate excitation wavelength, the fluorescent quantum efficiency, the shape of the excitation or emission spectrum, the excitation wavelength maximum, or the emission magnitude at any wavelength during, or at one or more times after excitation of the fluorescent moiety, the ratio of excitation amplitudes at two different wavelengths, the ratio of emission amplitudes at two different wavelengths, the excited state lifetime, the fluorescent anisotropy or any other measurable property of a fluorescent moiety and the like. Preferably fluorescent property refers to fluorescence emission, or the fluorescence emission ratio at two or more wavelengths.

The term "homolog" refers to two sequences or parts thereof, that are greater than, or equal to 75% identical when optimally aligned using the ALIGN program. Homology or sequence identity refers to the following. Two amino acid sequences are homologous if there is a partial or complete identity between their sequences. For example, 85% homology means that 85% of the amino acids are identical when the two sequences are aligned for maximum matching. Gaps (in either of the two sequences being matched) are allowed in maximizing matching; gap lengths of 5 or less are preferred with 2 or less being more preferred. Alternatively and preferably, two protein sequences (or polypeptide sequences derived from them of at least 30 amino acids in length) are homologous, as this term is used herein, if they have an alignment score of more than 5 (in standard deviation units) using the program ALIGN with the mutation data matrix and a gap penalty of 6 or greater. See Dayhoff, M.O., in *Atlas of Protein Sequence and Structure*, 1972, volume 5, National Biomedical Research Foundation, pp. 101–110, and Supplement 2 to this volume, pp. 1–10.

The term "modulates" refers to either the enhancement or inhibition (e.g. attenuation of the rate or efficiency) partially or complete of an activity or process.

The term "modulator" refers to a chemical compound (naturally occurring or non-naturally occurring), such as a biological macromolecule (e.g., nucleic acid, protein, non-peptide, or organic molecule), or an extract made from biological materials such as bacteria, plants, fungi, or animal (particularly mammalian, including human) cells or tissues. Modulators are evaluated for potential activity as inhibitors or activators (directly or indirectly) of a biological process or processes (e.g., agonist, partial antagonist, partial agonist, inverse agonist, antagonist, antineoplastic agents, cytotoxic agents, inhibitors of neoplastic transformation or cell proliferation, cell proliferation-promoting agents, and the like) by inclusion in screening assays described herein. The activity of a modulator may be known, unknown or partially known.

The term "non-naturally occurring" refers to the fact that an object cannot be found in nature. For example, a polypeptide or polynucleotide sequence that is present in an organism (including viruses) that can be isolated from a source in nature and which has not been intentionally modified by man in the laboratory is naturally-occurring, while such a sequence that has been intentionally modified by man is non-naturally occurring.

The term "optical property" refers to a physical property of light, including the molar extinction coefficient at an appropriate excitation wavelength, the fluorescent or luminescent quantum efficiency, the shape of the excitation spectrum or emission spectrum, the excitation wavelength maximum or emission wavelength maximum, the ratio of excitation amplitudes at two different wavelengths, the ratio of emission amplitudes at two different wavelengths, the excited state lifetime, the fluorescent anisotropy or any other measurable optical property of a compound, or any product or emission derived from that compound, either spontaneously or in response to electrical or chemical stimulation or reaction.

The term "polypeptide" refers to a polymer in which the monomers are amino acids and are joined together through amide bonds, alternatively referred to as a peptide. Additionally, unnatural amino acids, for example, beta-alanine, phenylglycine and homoarginine are also meant to be included. Commonly encountered amino acids, which are not gene-encoded, may also be used in the present invention. For a general review see Spatola, A. F., in *Chemistry and Biochemistry of Amino Acids, Peptides and Proteins*, B. Weinstein, eds., Marcel Dekker, New York, p. 267 (1983). All of the amino acids used in the present invention may be either the D- or L-isomer. The L-isomers are preferred. Chemically modified or substituted amino acids including phosphorylated, sulfated, methylated, or prenylated residues may also be used to create polypeptides for specific applications.

The term "post-translational type modification" refers to the enzymatic or non-enzymatic modification of an amino acid residue (preferably enzymatic). Such covalent modifications include phosphorylation, dephosphorylation glycosylation, methylation, sulfation, ubiquitination, prenylation and ADP-ribsoylation. Preferred post-translational type modifications include phosphorylation and dephosphorylation.

The term post-translational includes non-covalent type modifications including protein-protein interactions, and the binding of allosteric, or other modulators or second messengers such as calcium, or cAMP or inositol phosphates to the recognition motif.

The term "probe moiety" refers to a chemical moiety useful as a marker or indicator, or contrast agent for, absorption spectroscopy, luminescence spectroscopy, fluorescence spectroscopy, or magnetic detection.

The term "quencher" refers to a molecule or part of a compound that is capable of reducing the emission from a probe moiety. Such reduction includes reducing the light after the time when a photon is normally emitted from a fluorescent moiety. Quenching may occur by any of several mechanisms, including fluorescence resonance energy transfer, photoinduced electron transfer, paramagnetic enhancement of intersystem crossing, Dexter exchange coupling, and excitation coupling, such as the formation of dark complexes. Preferred quenchers include those that operate by fluorescence resonance energy transfer.

The term "recognition motif" refers to all or part of a polypeptide sequence recognized by a post-translational modification activity to enable a polypeptide to become modified by that post-translational modification activity. Typically, the affinity of a protein, e.g. enzyme, for the recognition motif is about 1 mM (apparent $K_d$), preferably a greater affinity of about 10 μM or less, more preferably, 1 μM or most preferably has an apparent $K_d$ of about 0.1 μM. The term is not meant to be limited to optimal or preferred recognition motifs, but encompasses all sequences that can specifically confer substrate recognition to a peptide. Preferably the recognition motif is a phosphorylated recognition motif (e.g. includes a phosphate group), or other post-translationally modified residues. Typically the recognition motif will, at least partially, comprise a protease site. The protease site may be located at any location within recognition motif.

The term "test chemical" refers to a chemical to be tested by one or more screening method(s) of the invention as a putative modulator. A test chemical can be any chemical, such as an inorganic chemical, an organic chemical, a protein, a peptide, a carbohydrate, a lipid, or a combination thereof. Usually, various predetermined concentrations of test chemicals are used for screening, such as 0.01 micromolar, 1 micromolar and 10 micromolar. Test chemical controls can include the measurement of a signal in the absence of the test compound or comparison to a compound known to modulate the target.

Introduction

The present invention recognizes for the first time that optical probes can be designed to measure a range of post-translational type activities. The advantages of the present invention include compositions that can be used in methods, particularly methods for high throughput and miniaturized screening systems for drug discovery and profiling. Optical probes provide for assays, that typically exhibit a large dynamic range, increased sensitivity and allow ratiometric readouts for the detection of post-translational type activities.

As a non-limiting introduction to the breadth of the invention, the invention includes several general and useful aspects, including:

1) A polypeptide moiety, which contains a recognition motif for a post translational type activity and a protease site, which is coupled to a first fluorescent moiety. Typically, the presence of a modification at the recognition motif alters protease activity at the protease site resulting in a modulation of the cleavage rate of the protease. Cleavage is sensed by a measurable change in at least one optical property of the optical probe upon cleavage at the protease site. In different embodiments, the invention may further comprise a second optical probe, such as fluorescent quencher or second fluorescent moiety or luminescent moiety. Typically the second optical probe is coupled to the polypeptide such that recognition motif and the protease site are located between them.

2) Methods for using the optical probes of (1) to determine whether a sample contains a post-translational type modification activity such as protein phosphorylation or dephosphorylation.

3) Methods for using the optical probes of (1) to determine whether a test chemical modulates the activity of a post-translational type activity.

4) Libraries of optical probes, each with a unique peptide sequence for use in selecting an optimal sequence specificity of a post-translational type activity.

5) A compound or therapeutic identified by at least one method of the present invention.

6) Systems for spectroscopic measurements using the optical probes (1) and methods above.

7) Microfluidic spectroscopic systems for using the optical probe (1) comprising at least one fluid containing structure with at least one electro-osmotic or electrophoretic system to control fluid movement within that structure.

These aspects of the invention and others described herein, can be achieved by using the methods and compositions of matter described herein. To gain a full appreciation of the scope of the invention, it will be further recognized that various aspects of the invention can be combined to make desirable embodiments of the invention. Such combinations result in particularly useful and robust embodiments of the invention.

Designing Peptide Sequences for Use in the Optical Probes of the Present Invention.

Generally peptide sequences for measuring a post-translational type activity encompass a post-translational recognition motif that contains a residue that, when modified, modulates the rate of cleavage of the substrate by a protease as compared to the unmodified form. Typically, such peptides contain a single scissile bond (bond that is cleaved within the substrate) for a specific protease and exhibit reasonable solubility (e.g. 0.1 mg/ml or greater) in aqueous solution. The design and size of peptide sequences for specific optical probes, and the choice of a particular protease, is dependent upon the application for which the optical probe is to be used. For example, for resonance energy transfer type applications, the peptide separating the fluorescent or luminescent moieties will typically be in the range of 5 to 50 amino acids in 5 length, preferably 10 to 25 amino acids in length, or more preferably 10 to 15 amino acids in length. For polarization based applications the peptide may be significantly larger, up to and including entire protein domains, for example 50 to 100 amino acids in length. Smaller peptides, in the range of 5 to 50 amino acids may also be used. Typically the protease site may be located at any position either completely or partially within the recognition motif. The recognition motif and protease site may be located at any position within the peptide with respect to the optical probe moiety. The section below describes the design of suitable peptide substrates for use in the present invention. Subsequent sections describe the selection and coupling of suitable fluorescent moieties for use in the invention. The following representative examples are offered by way of illustration, not by way of limitation.

A Design of Peptides for Measuring Protein Phosphorylation

In general protein kinases act on proteins via the addition of phosphate groups (phosphorylation) primarily on the amino acids, tyrosine, serine or threonine through a free hydroxyl group. The protein kinases that enzymatically catalyze these reactions may be classified into a number of distinct families based on shared structural and functional properties. Typically, kinases within a family have a similar overall topology, have similar modes of regulation and have similar substrate specificity's (see, Table 1, and may be used with the invention, as well as those recognition motifs developed in the future). For example, members of the AGC (protein kinase A, G or C) families of kinases typically prefer phosphorylation recognition motifs with basic amino acids (R or K), those in the CMGC group typically prefer proline containing motifs, etc. In Table 1, blank cells in the "Substrate Preference" column indicate that the complete information for every member of a particular class was not available, or indicates that the family was too small to define a clear substrate preference, or indicates that no clearly defined substrate preference yet exists.

Within sub-families, particular members have specific preferences for amino acids at specific positions within the substrate. These preferences have been extensively characterized for a number of kinases as described herein. Additional methods for identifying the substrate specificities and binding recognition motifs of new kinases are known in the art and may be used with the present invention. Such methods enable the substrate specificity of virtually any kinase known now, or discovered in the future, to be rapidly identified, for example see U.S. Pat. No. 5,532,167 by Cantley et al., issued Jul. 2, 1996, and PCT application WO 98/54577 by Lai et al., filed May 28, 1998.

TABLE 1

| MAIN GROUPS | SUB-GROUPS | DESCRIPTION | SUBSTRATE PREFERENCE |
|---|---|---|---|
| AGC GROUP | | | |
| | Group 1 | Cyclic nucleotide regulated protein kinase family | Arg/Lys Directed |
| | Group 2 | Diacylglycerol-activated/phospholipid-dependent protein kinase family | Arg/Lys Directed |
| | Group 3 | Related to protein kinase A and protein kinase C | Arg/Lys Directed |
| | Group 4 | Kinases that phosphorylate G protein coupled receptors | Negative charge Directed |
| | Group 5 | Budding yeast AGC-related protein kinases | Not available |
| | Group 6 | Kinases that phosphorylate ribosomal protein S6 family | Arg/Lys Directed |
| | Group 7 | Budding yeast DBF2/20 family | |
| | Group 8 | Flowering plant PVPK1 protein kinase homologue family | |
| | Group 9 | Other AGC related kinase families | Various |
| CAMK GROUP | | | |
| | CaMK Group 1 | Kinases regulated by $Ca^{2+}$/CaM and close relatives | Arg/Lys Directed |
| | CaMK Group 2 | CaMK group II | Arg/Lys Directed |
| | CaMK Other | Other CaMK related kinase families | Various |
| CMGC GROUP | | | |
| | CMGC Group 1 | Cyclic-dependent kinases (CDKS) and close relatives family | Ser/Pro Directed |
| | CMGC Group 2 | ERK (MAP) kinase family | Ser/Pro Directed |
| | CMGC Group 3 | Glycogen synthase kinase 3 family | Ser/Pro Directed |
| | CMGC Group 4 | Casein kinase II family | Negative charge directed |
| | CMGC Group 5 | Clk famiiy | |
| | CMGC Group 6 | CMGC Group other | Various |
| PTK GROUP I | | | |
| | | Non-membrane spanning protein tyrosine kinases | |
| | PTK Group 1 | Src family | IY directed |
| | PTK Group 2 | Tec/Atk family | |
| | PTK Group 3 | Csk family | IYM directed |
| | PTK Group 4 | Fes (Fps) family | IYE directed |
| | PTK Group 5 | Abl family | IYA directed |
| | PTK Group 6 | Syk/ZAP70 family | YE directed |
| | PTK Group 7 | Tyk2/Jak 1 family | |
| | PTK Group 8 | Ack family | |
| | PTK Group 9 | Focal adhesion kinase (Fak) family | |
| PTK GROUP 2 | | | |
| | | Membrane spanning protein tyrosine kinases | |
| | PTK Group 10 | Epidermal growth factor receptor family (EGF) | EEEYF directed (SEQ. ID NO.:54) |
| | PTK Group 11 | Eph/Elk/Eck receptor | |
| | PTK Group 12 | Axl family | |
| | PTK Group 13 | Tie/Tek family | |
| | PTK Group 14 | PDGF family | EEEYV directed (SEQ. ID NO.:55) |
| | PTK Group 15 | FGF family | EXYXF directed (SEQ. ID NO.:56) |
| | PTK Group 16 | Insulin receptor farruly | YMMM directed (SEQ. ID NO.:57) |
| | PTK Group 17 | LTK/ALK family | |
| | PTK Group 18 | Ros/Sevenless family | |
| | PTK Group 19 | Trk/Ror family | |
| | PTK Group 20 | DDR/TKT family | |
| | PTK Group 21 | Hepatocyte growth factor receptor family | |
| | PTK Group 22 | Nematode Kin 15/16 family | |
| | PTK Group 23 | Other membrane spanning kinases | Various |
| OPK GROUP | | | |

TABLE 1-continued

| MAIN GROUPS | SUB-GROUPS | DESCRIPTION | SUBSTRATE PREFERENCE |
|---|---|---|---|
| | | Other protein Kinases (not falling in major groups) | |
| | OPK Group 1 | Polo family | |
| | OPK Group 2 | MEK/STE7 family | |
| | OPK Group 3 | PAK/STE20 family | |
| | OPK Group 4 | MEKK/STE11 family | |
| | OPK Group 5 | NimA family | |
| | OPK Group 6 | Wee1/mik1 family | |
| | OPK Group 7 | Kinases involved in transcriptional control family | |
| | OPK Group 8 | Raf family | |
| | OPK Group 9 | Activin/TGFb receptor family | |
| | OPK Group 10 | Flowering plant putative receptor kinases and close relatives | |
| | OPK Group 11 | PSKIPTK "mixed lineage" leucine zipper domain family | |
| | OPK Group 12 | Casein kinase 1 family | |
| | OPK Group 13 | PKN prokaryotic protein kinase family | |
| | OPK Group 14 | Other protein kinase families (each with no close relatives) | Various |

Eukaryotic protein phosphatases are structurally and functionally diverse enzymes that are represented by three distinct gene families. Two of these, dephosphorylate phosphoserine and phosphothreonine residues, whereas the protein tyrosine phosphatases (PTPs) dephosphorylate phosphotyrosine amino acids. A subfamily of the PTPs, the dual specificity phosphatases, dephosphorylates all three phosphoamino acids. Within each family, the catalytic domains are highly conserved, with functional diversity endowed by regulatory domains and subunits.

The protein serine or threonine phosphatases type 1 and 2A account for as much as 95% of the phosphatase activity in cell extracts (Brautigan and Shriner, Methods. Enzymol. 159: 339–346 (1988). These enzymes have broad substrate specificities and may be regulated in vivo through targeting of the enzymes to discrete sub-cellular localizations.

The total number of protein tyrosine phosphatases encoded in the mammalian genome has been estimated at between 500 and approximately 2000. These estimates are imprecise due to the large number of sequence database entries that are different splice forms or duplicates of the same PTP sequence.

i) Tyrosine Phosphorylation or Dephosphorylation

Optical probes for detecting tyrosine kinase activity according to the present invention are designed by incorporating the desired phosphorylation motif into a peptide, and by ensuring that the only aromatic residue (Tyr, Trp or Phe) in the substrate is the tyrosine that is phosphorylated. It may also be preferable in certain cases to eliminate or reduce the number of negatively charged amino acids in the $P'_1$, $P'_2$ or $P'_3$ positions. If this is the case, then phosphorylation of the tyrosine residue by the tyrosine directed protein kinase activity modulates the rate of optical probe hydrolysis by chymotrypsin compared to the non-phosphorylated optical probe. The present inventors have recognized that elimination of negatively charged residues in the optical probe C-terminal to the scissile bond improves the efficiency of cleavage of non-phosphorylated optical probe, on occasion significantly increasing the utility of the optical probes for measuring kinase or phosphatase activities. This approach can be used to create specific optical probes for virtually all known tyrosine kinase activities by routine optimization of the reaction conditions as described herein. Specific illustrative examples for different tyrosine kinase classes are shown in Table 2, below for use with chymotrypsin.

TABLE 2

| Kinase | Optimal recognition motif for the kinase | Optical probe specific motif |
|---|---|---|
| c-FGR | MEEIYGIFF[2] (SEQ ID NO:30) | MEEIYGI*LS* SEQ. ID. NO:1 |
| Lyn | DEEIYEELE[2] (SEQ ID NO:31) | DEEIYES*LE* SEQ. ID. NO:2 |
| Src-1 | GEEEIYGEFEK[1] (SEQ ID NO:32) | GEEEIYGE*IEK* SEQ. ID. NO:3 |
| C-Abl | AXVIYAAPE[1] (SEQ ID NO:33) | AEAIYAAP*L* SEQ. ID. NO:4 |
| CSK | XEPIYMFF[2] (SEQ ID NO:34) | EPIYMLSL SEQ. ID. NO:5 |
| Insulin receptor | XEEEYMMMF[1] (SEQ ID NO:35) | EEEYMMM*M* SEQ. ID. NO:6 |
| PDGF receptor | EEEEYVFIX[1] (SEQ ID NO:36) | EEEEYVV*IX* SEQ. ID. NO:7 |
| EGF receptor | EEEEYFELV[1] (SEQ ID NO:37) | EEEEYV*LLV* SEQ. ID. NO:8 |
| FGF receptor | AEEEYFFLF[1] (SEQ ID NO:38) | AEEEYF*VLM* SEQ. ID. NO:9 |

In Table 2, bold residues indicate those considered to be significant in kinase recognition, and italicized residues are those that can be substituted to enable effective modulation of the proteolytic sensitivity of the optical probe towards chymotrypsin upon phosphorylation. The tyrosine that is phosphorylated is underlined, and the indicated references are (1) Songyang, et al., Current Biology 4:973–983, 1994, and (2) Ruzzene, et al., Eur. J. Biochem. 246: 433–439.

Optical probes for detecting protein tyrosine phosphatase activity according to the present invention are designed by incorporating the desired phosphorylation motif into a peptide, for example like those in (Table 2), or other such motifs developed now or in the future, and either enzymatically or chemically phosphorylating the appropriate amino acid. Dephosphorylation of the tyrosine residue in such optical probes by a tyrosine directed protein phosphatase activity modulates the rate of optical probe hydrolysis by chymotrypsin compared to the phosphorylated optical probe.

ii) Serine/Threonine Phosphorylation or Dephosphorylation

To develop optical probes for measuring serine or threonine kinase activities, peptides are designed to incorporate a single aromatic amino acid (Tyr, Trp or Phe) that is typically located within about three amino acids of a serine or threonine residue, which is phosphorylated by an appropriate serine or threonine specific kinase. It is also preferable in certain cases (depending on the protease selected) to eliminate or reduce the number of negatively charged amino acids (e.g. Asp or Glu residues) in the $P'_1$, $P'_2$ or $P'_3$ positions to ensure that the effect of phosphorylation of the serine or threonine residue provides a large modulation in proteolytic sensitivity of the optical probe upon phosphorylation. Examples of such sequences are provided in Table 3, below, for use with chymotrypsin.

designed by incorporating the desired phosphorylation motif into a peptide, for example like those in (Table 3), or other such motifs developed now or in the future, and either enzymatically or chemically phosphorylating the appropriate amino acid. Dephosphorylation of the serine or threonine residue in such an optical probe by a serine or threonine directed protein phosphatase activity modulates the rate of optical probe hydrolysis by chymotrypsin compared to the phosphorylated optical probe.

B Design of Peptides for Measuring Protein Prenylation.

Protein prenylation typically occurs through the addition of isoprenyl groups to cysteine residues located near the C-terminus of proteins. Typically the linkage of the isoprenyl moiety to cysteine occurs through the formation of a thioether with the cysteine sulfhydral. After the creation of the thioether intermediate, the modified protein may

TABLE 3

| Kinase | Optimal Motif | Optical probe with p-Ser in $P'_1$ | Optical probe with p-Ser in $P'_2$ |
|---|---|---|---|
| Protein kinase A | RRRRSIIFI[1] (SEQ ID NO:39) | RRRFSIIII SEQ ID NO:10 | RRFRSIIII SEQ. ID. NO:11 |
| Protein kinase C | RRRKFSFRRK[5] (SEQ ID NO:40) | RRRKFSLRRKA SEQ ID NO:12 | |
| CaMK I | LRRRLSDSNL[6] (SEQ ID NO:41) | LRRRFSASNL SEQ ID NO:13 | |
| CaMK II | KRQQSFDLE[2] (SEQ ID NO:42) | KRQFSIDLK SEQ ID NO:14 | KRFQSIDLK SEQ ID NO:15 |
| Casein kinase I | FDTGSIIFF[2] (SEQ ID NO:43) | GDQDTYSLLDK SEQ ID NO:16 | GDQDYLSLDK SEQ ID NO:17 |
| Casein kinase II | EDEESEDEE[2] (SEQ ID NO:44) | EDEFSEDEE SEQ ID NO:18 | EDFESEDEE SEQ ID NO:19 |
| CycA/cdk2 | HHHRSPRKR[1] (SEQ ID NO:45) | HHHFSPRKR SEQ ID NO:20 | HHFRSPRKR SEQ ID NO:21 |
| CycB/cdc2 | HHHKSPRRR[1] (SEQ ID NO:46) | HHHFSPRRR SEQ ID NO:22 | HHFKSPRRR SEQ ID NO:23 |
| ERK | RVDEPDSPGEK[1] (SEQ ID NO:47) | RVDEPFSPGEK SEQ ID NO:24 | |
| Glycogen Synthase | PRPASVPP[6] (SEQ ID NO:48) | PRPFSVPP SEQ ID NO:25 | |
| SLKI | RRFGSLRRF[1] (SEQ ID NO:49) | RRRFSLRRI SEQ ID NO:26 | RRFGSLRRI SEQ ID NO:27 |
| SRPK2 | RRRHSRRRR[3] (SEQ ID NO:50) | RRRFSRRRR SEQ ID NO:28 | RRFHSRRRR SEQ ID NO:29 |

In Table 3, bold residues indicate those considered to be significant in kinase recognition, and italicized residues are those that can be substituted to enable effective modulation of the proteolytic sensitivity of the optical probe towards chymotrypsin upon phosphorylation. The serine that is phosundergo proteolytic processing and cleavage to produce a product in which the cysteine is the C-terminal amino acid. A number of different isoprenylation activities have been identified that recognize distinct recognition motifs, as shown in Table 4.

TABLE 4

| Description of Activity | Recognition motif | Examples of proteins modified |
|---|---|---|
| Farnesyl transferase[1] | .......CAAX (SEQ. ID NO:51) | Lamins, p21$^{ras}$ |
| Type 1 geranylgeranyl transferase[1] | .......CAAL (SEQ. ID NO:52) | Smgp21B, G-protein γ-subunit |
| Type 2 geranylgeranyl transferase[1] | .......CXC or XCC (SEQ. ID NO:53) | Rab 3A | phorylated is underlined, and the indicated references are (1) Songyang, et al., Current Biology 4: 973–983, (1994), (2) Songyang, et al., Mol. Cell Biol. 16: 6486–6493, (1996), (3) Wang, et al., J. Cell Biol. 140: 737–750, (1998), and (4) Gonzalez et al., J. Biol. Chem., 266: 22159–22163, (1991). (5) Nishikawa et al., J. Biol. Chem. 272: 952–960 (1997), (6) Kemp and Pearson Meth. Enzymology 200: 121–155 (1991).

Optical probes for detecting protein serine or threonine phosphatase activity according to the present invention are (1) Clarke, S. (1992) Protein isoprenylation and methylation at carboxyl-terminal cysteine residues. Ann. Rev. Biochem. 61: 355–386, (2) Kawata et al., Post-translationally processed structure of the human platelet protein smg p21B: Evidence for geranylgeranylation and carboxyl methylation of the C-terminal cysteine. Proc. Natl. Acad. Sci. 87: 8960–8964 (1997). Optical probes for detecting protein prenylation activity according to the present invention are designed by incorporating the desired prenylation motif into a peptide, for example like those in (Table 4), or other such motifs developed now or in the future, usually within three amino acids of the C-terminus. Additional amino acids may be incorporated N-terminal to the cysteine reside that is modified to enable subsequent coupling of a first probe moiety, provided that they do not introduce additional prenylation sites. Under these circumstances, prenylation of the optical probe results in an increase in the rate of cleavage of the substrate upon exposure to an isoprenylated protein-specific endoprotease. Such a protease activity results in the cleavage of the substrate between the modified amino acid and the adjacent amino acid to liberate an intact tripeptide, and a new substrate with a C-terminal modified cysteine residue that results in a measurable change in at least one fluorescent property of the optical probe. Such a change can be used to measure protein prenylation activity as described in the section entitled "Assays using optical probes".

C Design of Peptides for Measuring Protein Glycosylation

In general, oligosaccharides may be either N-linked or O-linked to a protein or peptide. In the case of N-linked oligosaccharides, an N-acetylglucosamine residue is typically coupled to an asparagine residue. In the case of O-linked oligosaccharides, N-acetylgalactosamine is typically coupled to a serine or threonine residue. Optical probes for detecting N-linked protein glycosylation activity according to the present invention are designed by incorporating the desired glycosylation motif into a peptide, for example like those in (Table 5), or other such motifs developed now or in the future.

TABLE 5

| Glycosylation Activity | Consensus Sequence motif |
| --- | --- |
| N-glycosylation[1] | NXT or NXS |
| O-Glycosylation[2] | $X_1TPX_2P$ in preferred sequences |
| | $X_1$ = uncharged, and |
| | $X_2$ = small amino acids |

(1) Gooley et al., (1991) Biochem. Biophys. Res. Comm. 178: (3) 1194–201; and (2) Yoshida et al., (1997) J. Biol. Chem. 272: (27) 16884–8.

To provide the required modulation of proteolytic sensitivity of the substrate upon glycosylation the peptide should contain only one asparagine residue and no other basic amino acids such as lysine, arginine, histidine or glutamine residues. Under these conditions, the rate of cleavage of the substrate by trypsin is modulated by N-linked glycosylation of the asparagine residue in the substrate, which can be coupled to an optical readout using the methods described herein for example in the section entitled "Assays using opticalprobes".

Choice of Protease

Generally proteases for use in the present invention typically have the following characteristics: They are commonly available at high purity, are substantially stable, and recognize a substrate recognition motif that comprises at least one position in which the presence, or absence, of a post-translationally modified residue modulates the activity of the protease towards that substrate.

Preferred substrates possess well defined protease sites, and exhibit a significant modulation e.g. at least 2 fold, or more preferably at least 5 fold modulation of activity towards a post-translationally modified residue compared to a non-modified residue.

A Choice of Protease for Measuring Protein Phosphorylation

Proteases that may be used to measure peptide phosphorylation or dephosphorylation include those that recognize a substrate recognition motif that comprises at least one position in which the presence or absence of a phosphorylated residue modulates the activity of the protease towards that substrate. For example like those in (Table 6), or other such proteases developed now or in the future.

TABLE 6

| Name | EC number | Type | Peptide bond cleaved | Primary Specificity |
| --- | --- | --- | --- | --- |
| Caspase 3 | | Cysteine | $DXXD-P'_1$ (SEQ ID NO:58) | $P_1$ = Asp, $P'_1$ = neutral preferred |
| Cathepsin G | EC 3.4.21.20 | Serine | $P_1-P'_1$ | $P_1$ = aromatic preferred, W, Y, F |
| Chymotrypsin | EC 3.4.21.1 | Serine | $P_1-P'_1$ | $P_1$ = aromatic preferred, W, Y, F |
| Elastase | EC 3.4.21.36 | Serine | $P_1-P'_1$ | $P_1$ = uncharged, non aromatic, e.g. A, V, L, I, G, S, T $P'_1$ = non-specific |
| Endoproteinase Asp-N | | Unknown | $P_1$-Asp | $P'_1$ = Asp or $P'_1$ = Cysteic acid $P_1$ = non-specific |
| Endoproteinase Glu-N | EC 3.4.21.9 | Serine | $Glu-P'_1$ | $P_1$ = Glu or Asp $P'_1$ = non-specific |
| *Streptomyces griseus* GluSGP | EC 3.4.21.82 | Serine | $Glu-P'_1$ | $P_1$ = Glu or Asp $P'_1$ = non-specific |
| *Staphylococcus aureus* V8 | EC 3.4.21.19 | Serine | $Glu-P'_1$ | $P_1$ = Glu or Asp $P'_1$ = non-specific |

The flexibility in choice of phosphorylated amino acid (tyrosine, serine or threonine) combined with the flexibility in choice of the protease enables virtually any protein kinase or phosphatase activity to be measured using the present invention. It should be further noted that the above examples are illustrative of peptides that could be used to develop optical probes as described herein. Many other alternative substrates for a specific post-ranslational modification are possible by virtue of the inherent flexibility in the approach.

A contemplated version of the method is to use inducible controlling nucleotide sequences to produce a sudden increase in the expression of the protease within a cell, for the development of a cell based assay. An appropriate optical property would typically be monitored at one or more time intervals after the onset of increased expression of the protease.

B Choice of Proteaser for Measuring Protein Prenylation.

In the case of protein prenylation, proteases that exhibit modulated rates of cleavage of prenylated compared to non-prenylated substrates are preferred. For example, the yeast α factor maturation enzyme Ste24p Tam et al., (I1998) Dual roles for Ste24p in yeast $_\alpha$ factor maturation;NH2-terminal proteolysis and COOH-terminal CAAXprocessing. J. Biol. Chem. 142(3) 635-49; and the isoprenylated protein endoprotease; Ma et al., (1992) Substrate specificity of the isoprenylated protein endoprotease. Biochemistry 31 (47) 11772-7, or other such proteases developed now or in the future.

C Choice of Protease for Measuring Protein Glycosylation

Preferred proteases for use in the present invention to measure N-linked glycosylation include enzymes that primarily recognize basic amino acids that can be modified by either enzymatic or non-enzymatic glycosylation reactions to create modified substrates with modulated rates of cleavage compared to non-modified substrates. For example, bovine trypsin, porcine trypsin and pineapple bromelian or other such proteases developed now or in the future. (see, Casey and Lang (1976) Tryptic hydrolysis at asparagine residues in globulin chains. Biochim. Biophys. Acta 434: 184–8; Loh and Gainer, (1980) Evidence that glycosylation of pro-opiocortin and ACTH influences their proteolysis by trypsin and blood proteases. Mol. Cell. Endocrinol. (1) 35–44; Gil et al., (1991), Effect of non-enymatic glycosylation on reactivity in proteolysis. Acta Cient Venez 42: (1) 16–23.)

Choice of Probe Moieties

The choice of the probe moiety is governed by a number of factors including, the type of measurements being made, the availability of specific instrumentation and the ease of coupling of the probe moiety to the peptide. Additionally, other factors that are specific to a particular application are also relevant and include, the effect of labeling on the solubility of the peptide, kinetics of the optical probe with respect to the post-translational activity or protease, and the required detection sensitivity of the assay. Fortunately numerous probe moieties are commercially available or can be readily made so that availability of probe moieties to meet a desired situation is not limiting.

For fluorescent probes, preferred fluorophores typically exhibit good quantum yields, lifetimes, and extinction coefficients, are resistant to collisional quenching and bleaching, and should preferably be easily conjugated to the ligand. Particularly desirable, are fluorophores that show absorbance and emission in the red and near infrared range, which are useful in whole animal studies, because of reduced scattering background fluorescence, and greater transmission through tissues. Examples of such moieties include cyanines, oxazines, thiazines, porphyrins, phthalocyanines, fluorescent infrared-emitting polynuclear aromatic hydrocarbons such as violanthrones, fluorescent proteins, near IR squaraine dyes. (For example as shown in Dyes and Pigments, 17 19–27 (1991), U.S. Pat. No. 5,631, 169 to Lakowicz et al., issued May 20, 1997, and organometallic complexes such as the ruthenium and lanthanide complexes of U.S. Pat. Nos. 4,745,076 and 4,670,572, the disclosures of which are incorporated herein by reference). The lanthanide complexes have the advantage of not being quenched by oxygen, and the long lifetimes may allow easy suppression of the autofluorescence of biological samples.

Specific materials include fluoroscein isothicyanate (especially fluorescein-5-isothiocyanate), dichlorotriazinylaminofluorescein, tetramethylrhodamine-5 (and -6)-isothiocyanate, 1,3-bis-(2-dialkylamino-5-thienyl)-substituted squarines, and the succinimidyl esters of: 5 (and 6) carboxyfluoroscein; 5 (and 6)-carboxytetramethylrhodamine; and 7-amino-4-methylcoumarin-3-acetic acid. Semiconductor fluorescent nanocrystals are available with a range of emission spectra, are highly fluorescent and are also preferred, (see Bruchez et al., Science 281: 2013–2016).

Preferred luminescent probes include chemi-luminescent, electro-luminescent and bioluminescent compounds. Preferred bioluminescent compounds include bioluminescent proteins such as firefly, bacterial or click beetle luciferases, aequorins and other photoproteins, for example as described in U.S. Pat. Nos. 5,221,623, issued Jun. 22, 1989 to Thompson et al., and 5,683,888 issued Nov. 4, 1997 to Campbell, 5,674,713 issued Sep. 7, 1997 to DeLuca et al., 5,650,289 issued Jul. 22, 1997 to Wood and U.S. Pat. No. 5,843,746 issued Dec. 1, 1998 to Tatsumi et al. Preferred electro-luminescent probes include ruthenium complexes, as for example described in U.S. Pat. No. 5,597,910 issued to Jan. 28, 1997 to Gudibande. Preferred chemi-luminescent substrates include those based on 1,2-dioxetanes, as for example described in U.S. Pat. Nos. 4,372,745 issued Feb. 8, 1983 to Mandle et al., 5,656,207 issued Aug. 12, 1997 to Woodhead et al., and 5,800,999 issued Sep. 1, 1998 issued to Bronstein et al.

Preferred probes for use as NMR contrast agents include chelates of paramagnetic, ferromagnetic or diamagnetic metal ions complexed to lipophilic complexes as described in U.S. Pat. No. 5,628,982, issued May 13, 1997 to Lauffer et al. and U.S. Pat. No. 5,242,681, issued Sep. 7, 1993 to Elgavish et al., and fluorine-18-and 19 containing compounds J. Nucl. Med. 39 1884–91 (1998).

In some applications it may be desirable to derivatize the compounds above to render them more hydrophobic and permeable through cell membranes. The derivatizing groups should undergo hydrolysis inside cells to regenerate the compounds thus trapping them within cells. For this purpose, it is preferred that any phenolic hydroxyls or free amines in the dye structures are acylated with $C_1$–$C_4$ acyl groups (e.g. formyl, acetyl, n-butryl) or converted to various esters and carbonates, as described in Bundgaard, H., Design of Prodrugs, Elsevier Science Publishers (1985), Chapter 1, page 3 et seq., Further modification of the fluorescent moieties may also be accomplished, as required as described in U.S. Pat. No. 5,741,657 issued Apr. 21, 1998 to Tsien et al.

The probe may be attached to the polypeptide by a linker that provides a spacer between the probe and the peptide thereby preventing sterric interference of the probe on the interaction between the recognition motif and the post-translational-type activity. Preferred spacers are substantially stable under cellular conditions and easily coupled to the peptide and probe. Preferred examples include flexible aliphatic linkers such as γ-amino n-butyric acid (GABA), diaminopentane, and aminohexanoyl as well as rigid aromatic linkers. Such linkers are known in the art and described for example in the *Handbook of Fluorescent Probes and Research Chemicals*, by Richard Haugland, published by Molecular Probes.

Additionally non-covalent methods of attachment may also be used to label the peptide moiety. For example, the peptide may be designed to encompass a specific binding site for a fluorescent moiety as described in the pending U.S.

Patent applications, identified by Ser. No. 08/955,050, filed Oct. 21, 1997, entitled *Methods of using synthetic molecules and target sequences*, now U.S. Pat. No. 6,054,271; 08/955,859, filed Oct. 21, 1997, entitled *Synthetic molecules that specifically react with target sequences*, now U.S. Pat. No. 6,008,378, and 08/955,206, filed Oct. 21, 1997, entitled *Target sequences for synthetic molecules*, now U.S. Pat. No. 5,932,474. Labeling may then be achieved by incubation of the peptide with the membrane permeate fluorescent binding partner, which has the advantages of enabling the expression of peptides within intact living cells, and the subsequent labeling of these peptides in situ to create optical probes within intact living cells.

Fluorescent Proteins

For some cell based applications, preferred fluorescent moieties include endogenously fluorescent proteins, functional engineered fluorescent proteins, and homologs thereof. Because the entire fluorophore and peptide can be expressed within intact living cells without the addition of other co-factors or fluorophores, such optical probes provide the ability to monitor post-translational activities within defined cell populations, tissues or an entire transgenic organism. For example by the use of inducible controlling nucleotide sequences to produce a sudden increase in the expression of the optical probe and suitable protease. Endogenously fluorescent proteins have been isolated and cloned from a number of marine species including the sea pansies *Renilla reniformis, R. kollikeri* and *R. mullerei* and from the sea pens Ptilosarcus, Stylatula and Acanthoptilum, as well as from the Pacific Northwest jellyfish, Aequorea victoria; Szent-Gyorgyi et al. (SPIE conference 1999), D.C. Prasher et al., Gene, 111:229–233 (1992). These proteins are capable of forming a highly fluorescent, intrinsic chromophore through the cyclization and oxidation of internal amino acids within the protein that can be spectrally resolved from weakly fluorescent amino acids such as tryptophan and tyrosine.

Additionally fluorescent proteins have also been observed in other organisms, although in most cases these require the addition of some exogenous factor to enable fluorescence development. For example, the cloning and expression of yellow fluorescent protein from *Vibrio fischeri* strain Y-1 has been described by T. O. Baldwin et al., Biochemistry (1990) 29:5509–15.

This protein requires flavins as fluorescent co-factors. The cloning of Peridinin-chlorophyll a binding protein from the dinoflagellate Symbiodinium sp. was described by B. J. Morris et al., Plant Molecular Biology, (1994) 24:673:77. One useful aspect of this protein is that it fluoresces in red. The cloning of phycobiliproteins from marine cyanobacteria such as Synechococcus, e.g., phycoerythrin and phycocyanin, is described in S. M. Wilbanks et al., J. Biol. Chem. (1993) 268:1226–35. These proteins require phycobilins as fluorescent co-factors, whose insertion into the proteins involves auxiliary enzymes. The proteins fluoresce at yellow to red wavelengths.

A variety of mutants of the GFP from *Aequorea victoria* have been created that have distinct spectral properties, improved brightness and enhanced expression and folding in mammalian cells compared to the native GFP, Table 7, (*Green Fluorescent Proteins*, Chapter 2, pages 19 to 47, edited Sullivan and Kay, Academic Press, U.S. Pat. Nos: 5,625,048 to Tsien et al., issued Apr. 29, 1997; 5,777,079 to Tsien et al., issued Jul. 7, 1998; and U.S. Pat. No. 5,804,387 to Cormack et al., issued Sep. 8, 1998). In many cases these functional engineered fluorescent proteins have superior spectral properties to wild-type Aequorea GFP and are preferred for use in the optical probes of the invention.

TABLE 7

| Mutations | Common Name | Quantum Yield ($\Phi$) & Molar Extinction ($\epsilon$) | Excitation & Emission Max | Relative Fluorescence At 37° C. | Sensitivity To Low pH % max F at pH 6 |
|---|---|---|---|---|---|
| S65T type | | | | | |
| S65T, S72A, N149K, M153T, I167T | Emerald | $\Phi = 0.68$ $\epsilon = 57,500$ | 487 509 | 100 | 91 |
| F64L, S65T, V163A | | $\Phi = 0.58$ $\epsilon = 42,000$ | 488 511 | 54 | 43 |
| F64L, S65T (EGFP) | EGFP | $\Phi = 0.60$ $\epsilon = 55,900$ | 488 507 | 20 | 57 |
| S65T | | $\Phi = 0.64$ $\epsilon = 52,000$ | 489 511 | 12 | 56 |
| Y66H type | | | | | |
| F64L, Y66H, Y145F, V163A | P4-3E | $\Phi = 0.27$ $\epsilon = 22,000$ | 384 448 | 100 | N.D. |
| F64L, Y66H, Y145F | | $\Phi = 0.26$ $\epsilon = 26,300$ | 383 447 | 82 | 57 |
| Y66H, Y145F | P4-3 | $\Phi = 0.3$ $\epsilon = 22,300$ | 382 446 | 51 | 64 |
| Y66H | BFP | $\Phi = 0.24$ $\epsilon = 21,000$ | 384 448 | 15 | 59 |
| Y66W type | | | | | |
| S65T, Y66W, S72A N146I, M153T, V163A | W1C | $\Phi = 0.39$ $\epsilon = 21,200$ | 435 495 | 100 | 82 |
| F64L, S65T, Y66W, N146I, M153T, V163A | W1B | $\Phi = 0.4$ $\epsilon = 32,500$ | 434 452 476 (505) | 80 | 71 |
| Y66W, N146I, M153T, V163A | hW7 | $\Phi = 0.42$ $\epsilon = 23,900$ | 434 452 476 (505) | 61 | 88 |

TABLE 7-continued

| Mutations | Common Name | Quantum Yield (Φ) & Molar Extinction (ε) | Excitation & Emission Max | Relative Fluorescence At 37° C. | Sensitivity To Low pH % max F at pH 6 |
|---|---|---|---|---|---|
| Y66W | | | 436 485 | N.D. | N.D. |
| T203Y type | | | | | |
| S65G, S72A, K79R, T203Y | Topaz | Φ = 0.60 ε = 94,500 | 514 527 | 100 | 14 |
| S65G, V68L, S72A T203Y | 10C | Φ = 0.61 ε = 83,400 | 514 527 | 58 | 21 |
| S65G, V68L, Q69K S72A, T203Y | h10C+ | Φ = 0.71 ε = 62,000 | 516 529 | 50 | 54 |
| S65G, S72A, T203H | | Φ = 0.78 ε = 48,500 | 508 518 | 12 | 30 |
| S65G, S72A T203F | | Φ = 0.70 ε = 65,500 | 512 522 | 6 | 28 |
| T203I type | | | | | |
| T203I, S72A, Y145F | Sapphire | Φ = 0.64 ε = 29,000 | 395 511 | 100 | 90 |
| T203I T202F | H9 | Φ = 0.6 ε = 20,000 | 395 511 | 13 | 80 |

Cell Based Assays

Recombinant production of optical probes within living cells involves expressing nucleic acids having sequences that encode the fluorescent protein and substrate peptide as a fusion protein. In one embodiment described below, the optical probe comprises a first fluorescent protein, a peptide containing a post-translational modification recognition motif and a protease site, and a second fluorescent protein fused together as a single polypeptide chain. Nucleic acids encoding fluorescent proteins can be obtained by methods known in the art. For example, a nucleic acid encoding the protein can be isolated by polymerase chain reaction of cDNA from a suitable organism using primers based on the DNA sequence of the fluorescent protein. PCR methods are described in, for example, U.S. Pat. No. 4,683,195; Mullis et al. (1987) Cold Spring Harbor Symp. Quant. Biol. 51:263; and Erlich, ed., PCR *Technology*, (Stockton Press, N.Y., 1989).

Suitable clones expressing the optical probes of the invention may then be identified, isolated and characterized by fluorescence activated cell sorting (FACS) typically enabling the analysis of a few thousand cells per second.

The construction of expression vectors and the expression of genes in transfected cells involve the use of molecular cloning techniques also well known in the art. Sambrook et al., *Molecular Cloning—A Laboratory Manual*, Cold Spring Harbor Laboratory, Cold Spring Harbor, N.Y., (1989) and *Current Protocols in Molecular Biology*, F. M. Ausubel et al., eds., (Current Protocols, a joint venture between Greene Publishing Associates, Inc. and John Wiley & Sons, Inc., (most recent Supplement). Nucleic acids used to transfect cells with sequences coding for expression of the polypeptide of interest generally will be in the form of an expression vector including expression control sequences operatively linked to a nucleotide sequence coding for expression of the polypeptide comprising the optical probe.

Methods of Measurement

Methods that are preferred with the present invention include, fluorescence spectroscopy, luminescence spectroscopy, absorption spectroscopy and magnetic detection Fluorescent methods that are preferred with the present invention include, continuous or time resolved fluorescence spectroscopy, fluorescence correlation spectroscopy, fluorescence polarization spectroscopy, and resonance energy based fluorescence spectroscopy. Methods of performing such assays on fluorescent materials are well known in the art and are described in, e.g., Lakowicz, J. R., *Topics in Fluorescence Spectroscopy*, volumes 1 to 3, New York: Plenum Press (1991); Herman, B., Resonance energy transfer microscopy, in: Fluorescence Microscopy of Living Cells in Culture, Part B, Methods in Cell Biology, vol. 30, ed. Taylor, D. L. & Wang, Y.-L., San Diego: Academic Press (1989), pp. 219–243; Turro, N.J., *Modern Molecular Photochemistry*, Menlo Park: Benjamin/Cummings Publishing Col, Inc. (1978), pp. 296–361. The selection and use of specific fluorophores or quenchers for particular applications is known in the art, for example see, Berlman, I. B. Energy transfer parameters of aromatic compounds, Academic Press, New York and London (1973), that contains tables of spectral overlap integrals for the selection of resonance energy transfer partners. Additional information sources include the Molecular Probes Catalog, 1999; and Tsien et al., 1990 *Handbook of Biological Confocal Microscopy* pp. 169–178.

Assays Using Optical Probes

Methods for determining whether a sample has an activity typically involve contacting the sample with an optical probe, incubating the mixture under conditions to enable post translational modification of the substrate, and then adding a protease. Finally the degree of post-translational type activity in the sample is detected by determining at least one optical property of the optical probe or product thereof. In some cases, the optical probe and the protease may be added to a sample at the same time. Alternatively in the case where the sample contains cells, the method would typically involve stimulation of the cells, and then either lyzing the cells in the presence of the substrate, or in the case where the substrate is expressed within the cells, lyzing the cells in the presence of a protease to measure substrate modification. The method used to determine the degree of post-translational type activity is dependent on the assay format used.

In one aspect, the method may be based on the difference in fluorescence anisotropy of the optical probe before and after cleavage with a protease. In this case the optical probe typically comprises a polypeptide moiety, which contains a recognition motif for a post translational type activity and a protease site, which is coupled to a fluorescent moiety (FIG. 1). Modification of the polypeptide, by the post translational type activity, results in a modulation of the rate at which a protease cleaves the polypeptide which is sensed by a measurable change in fluorescence polarization of the optical probe upon cleavage.

Polarization measurements are based on the relative rotational movement of the fluorophore compared to the excited state life-time of that fluorophore. For globular molecules in dilute solution, the relationship between polarization (@) and the degree of rotational movement can be readily derived (see Weber, Polarization of the fluorescence of solutions, in Fluorescence and Phosphorescence Analysis, Don Hercules (ed.), Interscience Publishers New York. Chapter 8, pages 217–240 (1966)). Rotational movement can be related to the rotational diffusion constant of the molecule, and hence to the molecular volume. In practice there is a close correlation between the molecular size and relative polarization of emitted light from a fluorophore. As a consequence, a significant change in fluorescence polarization can occur when the optical probes of the present invention are acted upon by a protease. Polarization based measurements are relatively easy to set up, and can be obtained over a wide concentration, temperature, and ionic strength range.

In one embodiment of this method, fluorescence anisotropy measurements may be enhanced by attaching one end of the peptide to a solid matrix, or a bead. In either case, cleavage of the optical probe results in a larger drop in fluorescence polarization because of the increased rotational flexibility of the optical probe once separated from the solid matrix or bead.

In another aspect, the present invention takes advantage of resonance energy transfer either between two fluorescent moieties (FRET), or a bioluminescent moiety and fluorescent moiety (bioluminescent resonance energy transfer, BRET), or a fluorescent moiety and a quencher (resonance energy transfer, RET) to provide a fluorescent readout.

In FRET applications, the optical probe typically comprises a first fluorescent moiety and a second fluorescent moiety coupled to the polypeptide such that the recognition motif and the protease site are located between them (FIG. 1). In this case, cleavage of the polypeptide by a protease results in an alteration in energy transfer between the first fluorescent moiety and the second fluorescent moiety that may be used to determine post-translational activity. In this case, the fluorescent moieties are typically chosen such that the excitation spectrum of one of the moieties (the acceptor fluorescent moiety) overlaps with the emission spectrum of the donor fluorescent moiety. The donor fluorescent moiety is excited by light of appropriate intensity within the donor fluorescent moiety's excitation spectrum and under conditions in which direct excitation of the acceptor fluorophore is minimized. The donor fluorescent moiety then transfers the absorbed energy by non radiative means to the acceptor, which subsequently re-emits some of the absorbed energy as fluorescence emission, at a characteristic wavelength. FRET can be manifested as a reduction in the intensity of the fluorescent signal from the donor, reduction in the lifetime of its excited state, and an increase in emission of fluorescence from the acceptor fluorescent moiety. When the peptide substrate that connects the donor fluorescent moiety and acceptor fluorescent moiety is cleaved, the donor fluorescent moiety and the acceptor fluorescent moiety physically separate, and FRET is diminished or eliminated. Under these circumstances, fluorescence emission from the donor increases and fluorescence emission from the acceptor decreases.

The efficiency of FRET is dependent on the separation distance and the orientation of the donor fluorescent moiety and acceptor fluorescent moiety, the fluorescent quantum yield of the donor moiety and the energetic overlap with the acceptor moiety. Forster derived the relationship:

$$E=(F^O-F)/F^O=R_0^6/(R^6+R_0^6)$$

where E is the efficiency of FRET, F and $F^O$ are the fluorescence intensities of the donor in the presence and absence of the acceptor, respectively, and R is the distance between the donor and the acceptor. $R_0$, the distance at which the energy transfer efficiency is 50%, of maximum is given (in Å) by $$R_0=9.79\times10^3(K^2QJn^{-4})^{1/6}$$

where $K^2$ is an orientation factor having an average value close to 0.67 for freely mobile donors and acceptors, Q is the quantum yield of the unquenched fluorescent donor, n is the refractive index of the intervening medium, and J is the overlap integral, which expresses in quantitative terms the degree of spectral overlap, $$J=\int\infty_{0\epsilon\lambda}F_\lambda\lambda^4 d\lambda/\int\infty_0 F_\lambda d\lambda$$

where $\epsilon_\lambda$ is the molar absorptivity of the acceptor in $M^{-1}$ $cm^{-1}$ and $F_\lambda$ is the donor fluorescence at wavelength λ measured in cm. Forster, T. (1948) Ann.Physik 2: 55–75. The characteristic distance $R_0$ at which FRET is 50% efficient depends on the quantum yield of the donor, the extinction coefficient of the acceptor, the overlap between the donor's emission spectrum and the acceptor's excitation spectrum and the orientation factor between the two fluorophores.

Preferably, changes in the degree of FRET are determined as a function of the change in the ratio of the amount of fluorescence from the donor and acceptor moieties, a process referred to as "ratioing." By calculating the ratio, the assay is insensitive to fluctuations in substrate concentration, photobleaching and excitation intensity making the assay more robust. This is of particular importance in automated screening applications where the quality of the data produced is important for its subsequent analysis and interpretation.

A contemplated variation of the above assay is to either introduce, or express, the optical probe into living eukaryotic or prokaryotic cells to enable the measurement of intracellular post-translational activities.

In one aspect, the method would involve an optical probe comprising a first fluorescent protein, a peptide containing a post-translational modification recognition motif and a protease site, and a second fluorescent protein fused together as a single polypeptide chain. In this case the first fluorescent protein and the second fluorescent protein would be selected to enable FRET to occur as described above. A preferred pair of functional engineered fluorescent proteins for example being, Topaz (S65G, S72A, K79R, T203Y) and W1B (F64L, S65T, Y66W, N146I, M153T,V163A) (Table 7).

In another aspect the method would involve an optical probe comprising a peptide containing one or more binding sites for a fluorescent moiety, a post-translational modification recognition motif and a protease site. For example, the binding site could comprises a sequence that recognizes a fluorescent moiety as described in the pending U.S. Patent applications, identified by Ser. No. 08/955,050, filed Oct. 21, 1997, entitled *Methods of using synthetic molecules and target sequences*, now U.S. Pat. No. 6,054,271; 08/955,859, filed Oct. 21, 1997, entitled *Synthetic molecules that specifically react with target sequences*, now U.S. Pat. No. 6,008,378, and 08/955,206, filed Oct. 21, 1997, entitled *Target sequences for synthetic molecules*, now U.S. Pat. No. 5,932,474. In this case, expression of the peptide comprising the post-translational recognition motif, protease site and binding site could be accomplished using genetic means as described above. The addition of a membrane permeate fluorescent moiety capable of binding to the binding site would enable the creation, in situ of an optical probe.

In both cases, a contemplated version of the method is to use inducible controlling nucleotide sequences to produce a sudden increase in the expression of either the optical probe or the post-translational activity being assayed, e.g., by inducing expression of the construct. A suitable protease could be expressed within the cell, or induced, or introduced using a membrane translocating sequence U.S. Pat. No. 5,807,746, issued Sep. 15, 1998 to Lin et al. The efficiency of FRET is typically monitored at one or more time intervals after the onset of increased expression of the protease.

In another aspect the method would involve the introduction of an optical probe of the present invention into the cell through the use of a membrane translocating sequence, as described herein.

In BRET applications, the optical probe typically comprises a luminescent moiety and a fluorescent moiety coupled to the polypeptide such that the recognition motif and the protease site are located between them (FIG. 1). In this case, cleavage of the polypeptide by a protease results in an alteration in energy transfer between the luminescent moiety and the fluorescent moiety that may be used to determine post-translational type activities. In this case, the luminescent and fluorescent moieties are typically chosen such that the emission spectrum of the luminescent moiety overlaps with the excitation spectrum of the fluorescent moiety. Because the luminescent moiety provides light through a chemi-luminescent, electro-luminescent or bioluminescent reaction, there is no requirement for direct light excitation to create the excited state in the luminescent moiety. Instead appropriate substrates, or voltage must be provided to the luminescent moiety, to create an excited state within the luminescent moiety. In the case of bioluminescent proteins, such substrates are, generically referred to as luciferins (for example see U.S. Pat. No. 5,650,289 issued Jul. 22, 1997 to Wood). If BRET occurs, the energy from the excited state of the luminescent moiety is transferred to the fluorescent moiety by non radiative means, rather than being emitted as light from the luminescent moiety. Because the luminescent and fluorescent moieties emit light at characteristic wavelengths, the emission ratio of the two can provide a ratiometric readout as described for FRET based applications. BRET can be manifested as a reduction in the intensity of the fluorescent signal from the luminescent moiety, reduction in the lifetime of its excited state, and an increase in emission of fluorescence from the fluorescent moiety. When the peptide substrate that connects the luminescent moiety and fluorescent moiety is cleaved, the luminescent moiety and the fluorescent moiety physically separate, and BRET is diminished or eliminated. Under these circumstances light emission from the luminescent moiety increases and fluorescence emission from the fluorescent moiety decreases. The efficiency of BRET is dependent on the same separation and orientation factors as described above for FRET.

In RET applications, the optical probe typically comprises a first fluorescent moiety and a quencher moiety coupled to the polypeptide such that the recognition motif and the protease site are located between them (FIG. 1). In this case, cleavage of the polypeptide by a protease results in an alteration in energy transfer between the first fluorescent moiety and the quencher moiety that may be used to determine post-translational activity. In this case, the fluorescent moiety and the quencher moiety are typically chosen such that the absorption spectrum of one of the quencher (the acceptor moiety) overlaps with the emission spectrum of the donor fluorescent moiety. The donor fluorescent moiety is excited by light of appropriate intensity within the donor fluorescent moiety's excitation spectrum. The donor fluorescent moiety then transfers the absorbed energy by non radiative means to the quencher, which in this case does not re-emit any of the absorbed energy as light. RET can be manifested as a reduction in the intensity of the fluorescent signal from the donor or a reduction in the lifetime of its excited state. When the peptide substrate that connects the donor fluorescent moiety and quencher moiety is cleaved, the donor fluorescent moiety and the quencher moiety physically separate, and RET is diminished or eliminated. Under these circumstances fluorescence emission from the fluorescent moiety increases.

The post-translational modification assays of the present invention can be used in drug screening assays to identify compounds that alter a post translational type activity. In one embodiment, the assay is performed on a sample in vitro (e.g. in a sample isolated from a cell, or cell lysate or purified enzyme) containing the activity. A sample containing a known amount of activity is mixed with an optical probe of the invention and with a test chemical. The amount of the activity in the sample is then determined after addition of a protease as described herein, for example, by determining at least one optical property of the probe. Then the optical property of the sample in the presence of the test chemical is compared with the optical property of the sample in the absence of the test compound. A difference indicates that the test compound alters the activity.

In another embodiment, the ability of a test chemical to alter a post-translational type activity, in a cell based assay may be determined. In these assays, cells transfected with an expression vector encoding an optical probe of the invention, as described above, are exposed to different amounts of the test chemical, and the effect on FRET or fluorescence polarization in each cell can be determined after induction or introduction of a suitable protease. Typically, as with any method of the present invention, the difference in FRET or polarization of treated cells is compared to that of untreated controls.

Additionally libraries of optical probes can be created by producing peptides containing a diverse population of amino acid sequences. Such libraries are useful for the identification and characterization of novel post-translational type activities that have unknown or poorly defined substrate specificities.

As used herein, a "library" refers to a collection containing at least 5 different members, preferably at least 100 different members and more preferably at least 200 different members. The amino acid sequences for the peptide will typically be in the range or 10 to 20 amino acids in length and may be completely random or biased towards a particular sequence based on a particular structural motif, for example based on a known substrate for a particular post-translational activity. In some instances the library will created genetically and the individual members expressed in bacterial or a mammalian cells. Suitable clones expressing the optical probes of the invention may then be identified, isolated and characterized by fluorescence activated cell sorting (FACS) typically enabling the analysis of a few thousand cells per second. Alternatively, the peptides may be chemically synthesized and individual members attached to a solid matrix and arranged within a two dimensional array.

Typically, the library will contain variable peptides in which only a few, e.g., one to ten, amino acid positions are varied, but in which the probability of substitution is very high. Typically each member of the optical probe library will contain a single defined protease site, and a variable post-translational type recognition motif, such that randomized sequences comply with the design considerations for the particular post-translational type activity (described above). In one embodiment the array includes systematically substituted amino acids attached to a substrate, as described in U.S. Pat. No. 5,770,456, issued Jun. 23, 1998 to Holmes.

Screening of the library to identify optimal substrates may be achieved by incubating the array with a sample containing the post-translational activity, adding an appropriate protease, and then detecting at least one optical property from each member of the library. Those library members that are more efficiently modified by the post-translational type activity may then be identified by the degree to which the optical property of each library member is altered after exposure to the post-translational activity.

Alternatively libraries of known recognition motifs may be created in order to create an activity profile of post-translational activities in a sample. In this case, screening of the library is used to characterize the relative post-translational activities within by incubating the array with a sample containing the post-translational activities, adding an appropriate protease, and then detecting at least one optical property from each member of the library. Those library members that are more efficiently modified after exposure to the sample may then be identified by the degree to which the optical property of each library member is altered after exposure to the sample to determine the post-translational activities present within the sample.

A System for Spectroscopic Measurements

The optical probes of the present invention can be used with various systems for spectroscopic measurement. In one embodiment, the system comprises: a reagent for an assay, and a device comprising at least one plate or container, preferably a multi-well platform, and a second platform to hold said plate or container for detecting a signal from a sample. The system can further comprise a detector, such as a detector appropriate for detecting a signal from a sample or a plate on in a container as such detectors are known in the art or are later developed. The system can comprise multiple plates or containers or multi-well platforms. In this context, a reagent for an assay includes any reagent useful to perform biochemical or biological in vitro or in vivo testing procedures, such as, for example, buffers, co-factors, proteins such as enzymes or proteases, carbohydrates, lipids, nucleic acids, active fragments thereof, organic solvents such as DMSO, chemicals, analytes, therapeutics, compositions, cells, antibodies, ligands, and the like. In this context, an active fragment is a portion of a reagent that has substantially the activity of the parent reagent. The choice of optical probe depends on the type of assay to be performed. For example, FRET based assays would typically comprise an optical probe with two fluorophores. Fluorescent polarization based assays would typically be completed with optical probes comprising one fluorescent moiety (FIG. 1).

The optical probes of the present invention are suited for use with systems and methods that utilize automated and integratable workstations for identifying modulators, and chemicals having useful activity. Such systems are described generally in the art (see, U.S. Pat. Nos: 4,000,976 to Kramer et al. (issued Jan. 4, 1977), 5,104,621 to Pfost et al. (issued Apr. 14, 1992), 5,125,748 to Bjornson et al. (issued Jun. 30, 1992), 5,139,744 to Kowalski (issued Aug. 18, 1992), 5,206,568 Bjornson et al. (issued Apr. 27, 1993), 5,350,564 to Mazza et al. (Sep. 27, 1994), 5,589,351 to Harootunian (issued Dec. 31, 1996), and PCT Application Nos: WO 93/20612 to Baxter Deutschland GMBH (published Oct. 14, 1993), WO 96/05488 to McNeil et al. (published Feb. 22, 1996), WO 93/13423 to Agong et al. (published Jul. 8, 1993) and PCT/US98/09526 to Stylli et al., filed May 14, 1998.

Typically, such a system includes: A) a storage and retrieval module comprising storage locations for storing a plurality of chemicals in solution in addressable chemical wells, a chemical well retriever and having programmable selection and retrieval of the addressable chemical wells and having a storage capacity for at least 100,000 addressable wells, B) a sample distribution module comprising a liquid handler to aspirate or dispense solutions from selected addressable chemical wells, the chemical distribution module having programmable selection of, and aspiration from, the selected addressable chemical wells and programmable dispensation into selected addressable sample wells (including dispensation into arrays of addressable wells with different densities of addressable wells per centimeter squared) or at locations, preferably pre-selected, on a plate, C) a sample transporter to transport the selected addressable chemical wells to the sample distribution module and optionally having programmable control of transport of the selected addressable chemical wells or locations on a plate (including adaptive routing and parallel processing), D) a reaction module comprising either a reagent dispenser to dispense reagents into the selected addressable sample wells or locations on a plate or a fluorescent detector to detect chemical reactions in the selected addressable sample wells or locations on a plate, and a data processing and integration module.

The storage and retrieval module, the sample distribution module, and the reaction module are integrated and programmably controlled by the data processing and integration module. The storage and retrieval module, the sample distribution module, the sample transporter, the reaction module and the data processing and integration module are operably linked to facilitate rapid processing of the addressable sample wells or locations on a plate. Typically, devices of the invention can process at least 100,000 addressable wells or locations on a plate in 24 hours. This type of system is described in the PCT application WO/98/52047 by Stylli et al., entitled "Systems and method for rapidly identifying useful chemicals in liquid samples."

If desired, each separate module is integrated and programmably controlled to facilitate the rapid processing of liquid samples, as well as being operably linked to facilitate the rapid processing of liquid samples. In one embodiment the invention provides for a reaction module that is a fluorescence detector to monitor fluorescence. The fluorescence detector is integrated to other workstations with the data processing and integration module and operably linked with the sample transporter. Preferably, the fluorescence detector is of the type described herein and can be used for epi-fluorescence. Other fluorescence detectors that are compatible with the data processing and integration module and the sample transporter, if operable linkage to the sample transporter is desired, can be used as known in the art or developed in the future. For some embodiments of the invention, particularly for plates with 96, 192, 384 and 864 wells per plate, detectors are available for integration into the system. Such detectors are described in U.S. Pat. No. 5,589,351 (Harootunian), U.S. Pat. No. 5,355,215 (Schroeder), U.S. Patent Application (serial number pending), entitled "Detector and Screening Device for Ion Channels" filed Jul. 17, 1998, and PCT patent application WO 93/13423 (Akong). Alternatively, an entire plate may be "read" using an imager, such as a Molecular Dynamics Fluor-Imager 595 (Sunnyvale, Calif.). Multi-well platforms having greater than 864 wells, including 3,456 wells, can also be used in the present invention (see, for example, the PCT Application PCT/US98/11061, filed Jun. 2, 1998. These higher density well plates require miniaturized assay volumes that necessitate the use of highly sensitivity assays that do not require washing. The present invention provides such assays as described herein.

In another embodiment, the system comprises a microvolume liquid handling system that uses electrokinetic forces to control the movement of fluids through channels of the system, for example as described in U.S. Pat. No. , 5,800,690 issued Sep. 1, 1998 to Chow et al, European patent application EP 0 810 438 A2 filed May 5, 1997, by Pelc et al. and PCT application WO 98/00231 filed Jun. 24, 1997 by Parce et al. These systems use "chip" based analysis systems to provide massively parallel miniaturized analysis. Such systems are preferred systems of spectroscopic measurements in some instances that require miniaturized analysis.

In another embodiment, the system may comprise a two dimensional array of optical probes dispersed on a substratum, for example as described in U.S. Patents Nos., 4,216,245 issued Aug. 5, 1980 to Johnson, 5,721,435 issued Feb. 24, 1998 to Troll, and 5,601,980 issued Feb. 11, 1997 issued to Gordon et al. Such a system provides the ability to rapidly profile large numbers of optical probes and or large numbers of samples in a simple, miniaturized high throughput format.

A Method for Identifying a Chemical, Modulartor or a Therapeutic

The optical probes of the present invention can also be used for testing a therapeutic for useful therapeutic activity or toxicological activity. A therapeutic is identified by contacting a test chemical suspected of having a modulating activity of a biological process or target with a biological process or target on a plate or in a container, such as at least one well of a multi-well platform, that also comprises an optical probe. The test chemical can be part of a library of test chemicals that is screened for activity, such as biological activity. The library can have individual members that are tested individually or in combination, or the library can be a combination of individual members. Such libraries can have at least two members, preferably greater than about 100 members or greater than about 1,000 members, more preferably greater than about 10,000 members, and most preferably greater than about 100,000 or 1,000,000 members. After appropriate incubation of the sample with the optical probe, a protease is added and at least one optical property (such as FRET or polarization) of the sample is determined and compared to a non-treated control. If the sample having the test chemical exhibits increased or decreased FRET or polarization relative to that of the control or background levels, then a candidate modulator has been identified The candidate modulator can be further characterized and monitored for structure, potency, toxicology, and pharmacology using well-known methods. The structure of a candidate modulator identified by the invention can be determined or confirmed by methods known in the art, such as mass spectroscopy. For putative modulators stored for extended periods of time, the structure, activity, and potency of the putative modulator can be confirmed.

Depending on the system used to identify a candidate modulator, the candidate modulator will have putative pharmacological activity. For example, if the candidate modulator is found to inhibit a protein tyrosine phosphatase involved, for example in T-cell proliferation in vitro, then the candidate modulator would have presumptive pharmacological properties as an immunosuppressant or anti-inflammatory (see, Suthanthiran et al., Am. J. Kidney Disease, 28:159–172 (1996)). Such nexuses are known in the art for several disease states, and more are expected to be discovered over time. Based on such nexuses, appropriate confirmatory in vitro and in vivo models of pharmacological activity, as well as toxicology, can be selected. The optical probes, and methods of use described herein, enable rapid pharmacological profiling to assess selectivity and specificity, and toxicity. This data can subsequently be used to develop new candidates with improved characteristics.

Bioavailability and Toxicology of Candidate Modulators

Once identified, candidate modulators can be evaluated for bioavailability and toxicological effects using known methods (see, Lu, *Basic Toxicology, Fundamentals, Target Organs, and Risk Assessment*, Hemisphere Publishing Corp., Washington (1985); U.S. Pat. Nos: 5,196,313 to Culbreth (issued Mar. 23, 1993) and U.S. Pat. No. 5,567,952 to Benet (issued Oct. 22, 1996). For example, toxicology of a candidate modulator can be established by determining in vitro toxicity towards a cell line, such as a mammalian i.e. human, cell line. Candidate modulators can be treated with, for example, tissue extracts, such as preparations of liver, such as microsomal preparations, to determine increased or decreased toxicological properties of the chemical after being metabolized by a whole organism. The results of these types of studies are often predictive of toxicological properties of chemicals in animals, such as mammals, including humans.

The toxicological activity can be measured using reporter genes that are activated during toxicological activity or by cell lysis (see WO 98/13353, published Apr. 2, 1998). Preferred reporter genes produce a fluorescent or luminescent translational product (such as, for example, a Green Fluorescent Protein (see, for example, U.S. Pat. No. 5,625,048 to Tsien et al., issued Apr. 29, 1998; U.S. Pat. No. 5,777,079 to Tsien et al., issued Jul. 7, 1998; WO 96/23810 to Tsien, published Aug. 8, 1996; WO 97/28261, published Aug. 7, 1997; PCT/US97/12410, filed Jul. 16, 1997; PCT/US97/14595, filed Aug. 15, 1997)) or a translational product that can produce a fluorescent or luminescent product (such as, for example, beta-lactamase (see, for example, U.S. Pat. No. 5,741,657 to Tsien, issued Apr. 21, 1998, and WO 96/30540, published Oct. 3, 1996)), such as an enzymatic degradation product. Cell lysis can be detected in the present invention as a reduction in a fluorescence signal from at least one photon-producing agent within a cell in the presence of at least one photon reducing agent. Such toxicological determinations can be made using prokaryotic or eukaryotic cells, optionally using toxicological profiling, such as described in PCT/US94/00583, filed Jan. 21, 1994 (WO 94/17208), German Patent No. 69406772.5-08, issued Nov. 25, 1997; EPC 0680517, issued Nov. 12, 1994; U.S. Pat. No.

5,589,337, issued Dec. 31, 1996; EPO 651825, issued Jan. 14, 1998; and U.S. Pat. No. 5,585,232, issued Dec. 17, 1996).

Alternatively, or in addition to these in vitro studies, the bioavailability and toxicological properties of a candidate modulator in an animal model, such as mice, rats, rabbits, or monkeys, can be determined using established methods (see, Lu, supra (1985); and Creasey, Drug Disposition in Humans, The Basis of Clinical Pharmacology, Oxford University Press, Oxford (1979), Osweiler, Toxicology, Williams and Wilkins, Baltimore, Md. (1995), Yang, Toxicology of Chemical Mixtures; Case Studies, Mechanisms, and Novel Approaches, Academic Press, Inc., San Diego, Calif. (1994), Burrell et al., Toxicology of the Immune System; A Human Approach, Van Nostrand Reinhld, Co. (1997), Niesink et al., Toxicology; Principles and Applications, CRC Press, Boca Raton, FL (1996)). Depending on the toxicity, target organ, tissue, locus, and presumptive mechanism of the candidate modulator, the skilled artisan would not be burdened to determine appropriate doses, $LD_{50}$ values, routes of administration, and regimes that would be appropriate to determine the toxicological properties of the candidate modulator. In addition to animal models, human clinical trials can be performed following established procedures, such as those set forth by the United States Food and Drug Administration (USFDA) or equivalents of other governments. These toxicity studies provide the basis for determining the therapeutic utility of a candidate modulator in vivo.

Efficacy of Candidate Modulators

Efficacy of a candidate modulator can be established using several art-recognized methods, such as in vitro methods, animal models, or human clinical trials (see, Creasey, supra (1979)). Recognized in vitro models exist for several diseases or conditions. For example, the ability of a chemical to extend the life-span of HIV-infected cells in vitro is recognized as an acceptable model to identify chemicals expected to be efficacious to treat HIV infection or AIDS (see, Daluge et al., Antimicro. Agents Chemother, 41:1082–1093 (1995)). Furthermore, the ability of cyclosporin A (CsA) to prevent proliferation of T-cells in vitro has been established as an acceptable model to identify chemicals expected to be efficacious as immunosuppressants (see, Suthanthiran et al., supra, (1996)). For nearly every class of therapeutic, disease, or condition, an acceptable in vitro or animal model is available. Such models exist, for example, for gastro-intestinal disorders, cancers, cardiology, neurobiology, and immunology. In addition, these in vitro methods can use tissue extracts, such as preparations of liver, such as microsomal preparations, to provide a reliable indication of the effects of metabolism on the candidate modulator. Similarly, acceptable animal models may be used to establish efficacy of chemicals to treat various diseases or conditions. For example, the rabbit knee is an accepted model for testing chemicals for efficacy in treating arthritis (see, Shaw and Lacy, J. Bone Joint Surg. (Br) 55:197–205 (1973)). Hydrocortisone, which is approved for use in humans to treat arthritis, is efficacious in this model which confirms the validity of this model (see, McDonough, Phys. Ther. 62:835–839 (1982)). When choosing an appropriate model to determine efficacy of a candidate modulator, the skilled artisan can be guided by the state of the art to choose an appropriate model, dose, and route of administration, regime, and endpoint and as such would not be unduly burdened.

In addition to animal models, human clinical trials can be used to determine the efficacy of a candidate modulator in humans. The USFDA, or equivalent governmental agencies, have established procedures for such studies.

Selectivity of Candidate Modulators

The in vitro and in vivo methods described above also establish the selectivity of a candidate modulator. It is recognized that chemicals can modulate a wide variety of biological processes or be selective. Panels of enzymes or panels of cells based on the present invention, or a combination of both, can be used to determine the specificity of the candidate modulator. Selectivity is evident, for example, in the field of chemotherapy, where the selectivity of a chemical to be toxic towards cancerous cells, but not towards non-cancerous cells, is obviously desirable. Selective modulators are preferable because they have fewer side effects in the clinical setting. The selectivity of a candidate modulator can be established in vitro by testing the toxicity and effect of a candidate modulator on a plurality of cell lines that exhibit a variety of cellular pathways and sensitivities. The data obtained from these in vitro toxicity studies can be extended into in vivo animal model studies, including human clinical trials, to determine toxicity, efficacy, and selectivity of the candidate modulator suing art-recognized methods.

For example arrays of kinase or phosphatase optical probes may be used to rapidly profile the selectivity of a test chemical with respect to its ability to inhibit related kinases or phosphatases. Such arrays may be located within a microtiter plate, or as a printed array, for example as disclosed in U.S. Pat. Nos., 4,216,245 issued Aug. 5, 1980 to Johnson, 5,721,435 issued Feb. 24, 1998 to Troll, and 5,601,980 issued Feb. 11, 1997 issued to Gordon et al. Such a system provides the ability to rapidly profile large numbers of kinases or phosphatases in the presence or absence of a test chemical in order to profile in a simple, miniaturized high throughput format the selectivity of a candidate modulator.

An Identified Chemical, Modulator, or Therapeutic and Compositions

The invention includes compositions, such as novel chemicals, and therapeutics identified by at least one method of the present invention as having activity by the operation of methods, systems or components described herein. Novel chemicals, as used herein, do not include chemicals already publicly known in the art as of the filing date of this application. Typically, a chemical would be identified as having activity from using the invention and then its structure revealed from a proprietary database of chemical structures or determined using analytical techniques such as mass spectroscopy.

One embodiment of the invention is a chemical with useful activity, comprising a chemical identified by the method described above. Such compositions include small organic molecules, nucleic acids, peptides and other molecules readily synthesized by techniques available in the art and developed in the future. For example, the following combinatorial compounds are suitable for screening: peptoids (PCT Publication No. WO 91/19735, Dec. 26, 1991), encoded peptides (PCT Publication No. WO 93/20242, Oct. 14, 1993), random bio-oligomers (PCT Publication WO 92/00091, Jan. 9, 1992), benzodiazepines (U.S. Pat. No. 5,288,514), diversomeres such as hydantoins, benzodiazepines and dipeptides (Hobbs DeWitt, S. et al., Proc. Nat. Acad. Sci. USA 90: 6909–6913 (1993)), vinylogous polypeptides (Hagihara et al., J. Amer. Chem. Soc. 114:

6568 (1992)), nonpeptidal peptidomimetics with a Beta-D-Glucose scaffolding (Hirschmann, R. et al., J. Amer. Chem. Soc. 114: 9217–9218 (1992)), analogous organic syntheses of small compound libraries (Chen, C. et al., J. Amer. Chem. Soc. 116:2661 (1994)), oligocarbamates (Cho, C.Y. et al., Science 261: 1303 (1993)), and/or peptidyl phosphonates (Campbell, D.A. et al., J. Org. Chem. 59: 658 (1994)). See, generally, Gordon, E. M. et al., J. Med Chem. 37: 1385 (1994). The contents of all of the aforementioned publications are incorporated herein by reference.

The present invention also encompasses the identified compositions in a pharmaceutical composition comprising a pharmaceutically acceptable carrier prepared for storage and subsequent administration, which have a pharmaceutically effective amount of the products disclosed above in a pharmaceutically acceptable carrier or diluent. Acceptable carriers or diluents for therapeutic use are well known in the pharmaceutical art, and are described, for example, in Remington's Pharmaceutical Sciences, Mack Publishing Co. (A. R. Gennaro edit. 1985). Preservatives, stabilizers, dyes and even flavoring agents may be provided in the pharmaceutical composition. For example, sodium benzoate, acsorbic acid and esters of p-hydroxybenzoic acid may be added as preservatives. In addition, antioxidants and suspending agents may be used.

The compositions of the present invention may be formulated and used as tablets, capsules or elixirs for oral administration; suppositories for rectal administration; sterile solutions, suspensions for injectable administration; and the like. Injectables can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, and the like. In addition, if desired, the injectable pharmaceutical compositions may contain minor amounts of nontoxic auxiliary substances, such as wetting agents, pH buffering agents, and the like. If desired, absorption enhancing preparations (e.g., liposomes), may be utilized.

The pharmaceutically effective amount of the composition required as a dose will depend on the route of administration, the type of animal being treated, and the physical characteristics of the specific animal under consideration. The dose can be tailored to achieve a desired effect, but will depend on such factors as weight, diet, concurrent medication and other factors which those skilled in the medical arts will recognize. In practicing the methods of the invention, the products or compositions can be used alone or in combination with one another, or in combination with other therapeutic or diagnostic agents. These products can be utilized in vivo, ordinarily in a mammal, preferably in a human, or in vitro. In employing them in vivo, the products or compositions can be administered to the mammal in a variety of ways, including parenterally, intravenously, subcutaneously, intramuscularly, colonically, rectally, nasally or intraperitoneally, employing a variety of dosage forms. Such methods may also be applied to testing chemical activity in vivo.

As will be readily apparent to one skilled in the art, the useful in vivo dosage to be administered and the particular mode of administration will vary depending upon the age, weight and mammalian species treated, the particular compounds employed, and the specific use for which these compounds are employed. The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved. Alternatively, acceptable in vitro studies can be used to establish useful doses and routes of administration of the compositions identified by the present methods using established pharmacological methods.

In non-human animal studies, applications of potential products are commenced at higher dosage levels, with dosage being decreased until the desired effect is no longer achieved or adverse side effects disappear. The dosage for the products of the present invention can range broadly depending upon the desired affects and the therapeutic indication. Typically, dosages may be between about 10 mg/kg and 100 mg/kg body weight, and preferably between about 100 g/kg and 10 mg/kg body weight. Administration is preferably oral on a daily basis.

The exact formulation, route of administration and dosage can be chosen by the individual physician in view of the patient's condition. (See e.g., Fingl et al., in *The Pharmacological Basis of Therapeutics*, 1975). It should be noted that the attending physician would know how to and when to terminate, interrupt, or adjust administration due to toxicity, or to organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Depending on the specific conditions being treated, such agents may be formulated and administered systemically or locally. Techniques for formulation and administration may be found in *Remington's Pharmaceutical Sciences*, 18th Ed., Mack Publishing Co., Easton, Pa. (1990). Suitable routes may include oral, rectal, transdermal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections.

For injection, the agents of the invention may be formulated in aqueous solutions, preferably in physiologically compatible buffers such as Hanks' solution, Ringer's solution, or physiological saline buffer. For such transmucosal administration, penetrants appropriate to the barrier to be permeated are used in the formulation. Such penetrants are generally known in the art. Use of pharmaceutically acceptable carriers to formulate the compounds herein disclosed for the practice of the invention into dosages suitable for systemic administration is within the scope of the invention. With proper choice of carrier and suitable manufacturing practice, the compositions of the present invention, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a patient to be treated.

Agents intended to be administered intracellularly may be administered using techniques well known to those of ordinary skill in the art. For example, such agents may be encapsulated into liposomes, then administered as described above. All molecules present in an aqueous solution at the time of liposome formation are incorporated into the aqueous interior. The liposomal contents are both protected from the external micro-environment and, because liposomes fuse with cell membranes, are efficiently delivered into the cell cytoplasm. Additionally, due to their hydrophobicity, small organic molecules may be directly administered intracellularly.

Pharmaceutical compositions suitable for use in the present invention include compositions wherein the active ingredients are contained in an effective amount to achieve its intended purpose. Determination of the effective amounts is well within the capability of those skilled in the art, especially in light of the detailed disclosure provided herein. In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions. The pharmaceutical compositions of the present invention may be manufactured in a manner that is itself known, for example, by means of conventional mixing, dissolving, granulating, dragee-making, levitating, emulsifying, encapsulating, entrapping, or lyophilizing processes.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses. Such formulations can be made using methods known in the art (see, for example, U.S. Pat. Nos. 5,733,888 (injectable compositions); 5,726,181 (poorly water soluble compounds); 5,707,641 (therapeutically active proteins or peptides); 5,667,809 (lipophilic agents); 5,576,012 (solubilizing polymeric agents); 5,707,615 (anti-viral formulations); 5,683,676 (particulate medicaments); 5,654,286 (topical formulations); 5,688,529 (oral suspensions); 5,445,829 (extended release formulations); 5,653,987 (liquid formulations); 5,641,515 (controlled release formulations) and 5,601,845 (spheroid formulations).

EXAMPLES

The following examples are offered by way of illustration, not by way of limitation.

Example 1

Measurement of Tyrosine Kinase Activity Using Optical Probes.

Peptides were prepared by traditional solid-phase synthesis see, Merrifield, J. Amer. Chem. Soc., 85:2149–2154 (1963); Fields, G. B., et al, Principles and practice of solid-phase peptide synthesis, pages 77–183 in *Synthetic Peptides: A Users Guide*, Grant, G. R., ed., W. H. Freeman and Co. New York, (1992), in conjunction with the "tea-bag" methodology using Boc/benzyl based chemistry. See, Houghten et al., Proc. Natl. Acad. Sci. USA 82:513–5135 (1985). Peptides were assembled on methylbenzhydrylamine resin (MBHA resin) using traditional Boc/Benzyl based chemistry. A minor modification to the protocol (in the case of the abl-specific substrate (AEAIYAAPL, SEQ. I.D. No. 4) was the use of a base sensitive protecting group (Fmoc) for the side chain of the C-terminal lysine residue. Bags, made of a polypropylene mesh material were filled with MBHA resin. The bags ("tea-bags") were placed in a Nalgene™ bottle with dichloromethane (DCM), enough to cover the bags, and shaken 5 min to allow the swelling of the resin. The DCM solution was then discarded and the actual synthesis was carried out. (All subsequent steps involved the addition of enough solvent to cover all the bags and vigorous shaking to ensure adequate solvent transfer).

The bags were washed 3 times, first with 5% diisopropylethylamine (DIEA) in DCM (neutralization step) for 2 minutes, and then twice with 100% DCM (each for one minute) to remove excess base. After neutralization, the bags were sorted and placed into a NalgeneM bottle containing a solution of the amino acid of interest in DCM, an equal amount of diisopropylcarbodiimide (DIC) in DCM was added to activate the coupling reaction. A 5-fold excess of amino acid and DIC was used for all of the couplings. The bottle was shaken for one hour to ensure completion of the reaction. The reaction mixture was discarded and the packets were washed in DMF twice for 1 minute to remove excess amino acids and by-products like diisopropylurea. Two final washes with DCM were performed to remove any excess DMF. The N-α-t-Boc was removed by acidolysis using a solution of 55% TFA in DCM for 30 minutes leaving the TFA salt of the α-amino group. The bags were washed successively with DCM (1×1 minute), isopropanol (2×1 minute) and DCM (1×1 minute). The synthesis was completed by repeating the same procedure while substituting for the corresponding amino acid at the coupling step.

After removal of the N-α-t-Boc from the γ-Amino-n-butyric acid (GABA), the bags were washed 3 times, 2 minutes each, with 5% DIEA in DCM, then with DCM (3×2 minutes). The bags were sorted, placed in a Nalgene™ bottle containing a solution of fluorescein isothiocyanate (FITC) in DCM/DMF (80/20) and shaken for 2 minutes (2-fold excess). Neat DIEA was then added to the FITC solution. The bottle was shaken for 3 hours to ensure completion of the reaction. The reaction mixture was discarded and the bags were washed in DCM (4×2 minutes) and DMF (1×2 minutes).

The Fmoc group on the side chain of the C-terminal lysine residue was removed using a solution of 20% piperidine in DMF for 25 minutes. The bags were washed successively with DMF (2×2 minutes), DCM (1×2 minutes) and DMF (1×2 minutes). Bags were then placed in a Nalgene™ bottle containing a solution of 7-hydroxycoumarin-3-carboxylic acid (1.5-fold excess) in DMF and shaken for 2 minutes. A solution of PyBop/HOBt in DMF was added to the bottle and the mixture was shaken for 2 minutes. Neat DIEA was then added and the mixture was shaken for 2 hours. The reaction mixture was discarded, the packets were washed with DMF (3×2 minutes) and DCM (3×2 minutes), and placed in a desiccator and dried under vacuum in preparation for cleavage.

All peptides were side chain deprotected and cleaved from the resin at 0° C. with liquid HF in presence of anisole as a carbocation scavenger. The reaction was allowed to proceed for 60 minutes. Liquid HF was then removed using a strong flow of $N_2$ for 90 minutes followed by the use of aspirator vacuum for 60 minutes while maintaining the temperature at 0° C. The reaction vessels were removed from the apparatus and the residual anisole was removed with two ethylether washes. The peptides were extracted with two 30 ml 10% AcOH washes. For each peptide, the extraction solutions were pooled and lyophilized. The crude peptides were weighed and stored under nitrogen to await purification.

Automated Peptide Synthesis.

Alternatively, fluorescent peptide substrates were made using an automated peptide synthesizer (ABI 432A, Applied Biosystems, Foster City, Calif.) using Fmoc/ t-Boc chemistry. See Fields, G. B., et al., Principles and practice of solid-phase peptide synthesis, pages 77–183 in *Synthetic Peptides: A Users Guide*, Grant, G. R., ed., W. H. Freeman and Co. New York, (1992). Briefly, after the automated peptide synthesis of the desired peptide (containing an unprotected N-terminal GABA and a Fmoc protected C-terminal lysine) was complete, the synthesis column was removed from the ABI432A synthesizer. The column containing the peptide attached to the resin was manually flushed with DMF to swell the resin. A two ml solution of 100 μM FITC (5 fold excess) in 10% DIEA/DMF was then slowly injected through the synthesis column over a period of 2 hours using a syringe pump. The synthesis column was washed with (5×10 ml) DMF and THF (3×5 ml) and finally dried with a stream of dry nitrogen. The dried resin was suspended in 1 ml of trifluoroacetic (TFA) containing 50 μl of ethanedithiol and 50 μl of thioanisole, this mixture was stirred under nitrogen for 4 hours. The peptide was precipitated from the TFA solution by the addition of 20 ml of ether. The solid was further washed with ether (3×20 ml) to remove the thiol scavengers. The precipitated peptide (still mixed with the cleaved resin) was dried under vacuum. Finally, the C-terminal lysine of the peptide (in the case of the abl-specific peptide (AEMYAAPL, SEQ. ID. NO: 4) was labeled with the N-hydroxysuccimidyl ester of 7-hydroxycoumarin-3-carboxylic acid (NHS-coumarin ester). This was accomplished by incubating a 5-fold excess of the NHS-coumarin ester with the peptide overnight at room temperature in a solution of DMF containing 10% DIEA. After removal of the solvent the peptide was purified as described below.

A fluorescein/rhodamine fluorescent substrate was produced using an identical procedure to that described above with the exception that an amine reactive rhodamine fluorophore (Lissamine rhodamine B sulfonyl chloride) was used to label the C-terminal lysine. Previous attempts to synthesize peptides with a C-terminal lysine labeled with rhodamine while the peptides were still attached to the resin were not successful. The method described above (labeling with rhodamine after cleavage from the resin) avoids the problematic tendency of rhodamine labels to bind irreversibly to the resins. Reaction of amine reactive rhodamine derivatives while the peptides are still attached to the resin apparently precludes them from reacting with the C-terminal lysine.

The crude peptides were purified by reversed-phase high-performance liquid chromatography on a $C_{18}$ column using established methods. The mobile phase solvents were 0.1% TFA in water (Solvent A) and 0.1% TFA in Acetonitrile (Solvent B). The fractions containing the purified material were pooled and lyophilized and the purified peptides were characterized by analytical reverse phase-HPLC and by mass spectral analysis. Peptide concentrations were determined by absorbance spectroscopy, using coumarin and fluorescein extinction coefficients of 35,000 and 75,000 $M^{-1}$ $cm^{-1}$, respectively. Peptides were stable at 4° C. for at least one month and indefinitely at –20° C.

Preparation of Phosphorylated Optical Probes.

To prepare a sample of phosphorylated optical probe, the peptides were incubated with excess tyrosine kinase activity for a sufficient time to ensure complete phosphorylation of the peptide. Typically for v -Abl kinase reactions, the reaction buffer consisted of: 0.1×phosphate buffered saline (PBS), 5 mM $MgCl_2$, 200 μM ATP and not more than 10% of the total reaction volume of the tyrosine kinase enzyme. Reaction volumes were typically 20 μL, but were also performed at 10 μL and 100 μL. Recombinant v-Abl kinase was typically purchased from Calbiochem. Kinase reactions were quenched by the addition of 20 mM EDTA, pH 8. The degree of phosphorylation of the peptide was monitored over time by removing samples of the reaction mixture and analyzing them by reverse-phase high-performance liquid chromatography.

Alternatively, phosphorylated optical probes could be prepared directly during the peptide synthesis by simply using the O-benzyl protected phosphate derivative of the desired hydroxyl containing amino acid. For example, N α-Fmoc-O-benzyl-L-phosphotyrosine is commercially available and is compatible with standard Fmoc solid phase peptide synthesis. See White, P. et al. in "*Innovations & Perspectives in Solid Phase Synthesis and Combinatorial Libraries, 4th International Symposium*", R. Epton (Ed.), Mayflower Scientific Ltd. Birmingham, (1966), pp557. Thus, phosphorylated optical probes could be readily produced using protocols similar to those described above for automated peptide synthesis using Fmoc chemistry and purified as described below.

For example, using a Dionex HPLC apparatus and a C18 reverse-phase column by running a gradient elution profile consisting of either 5 to 80% acetonitrile/0.1% trifluoroacetic acid (~pH 3) or 5 to 80% acetonitrile/0.1% triethylamine (~pH 7.5) over 25 minutes. Alternatively, the degree of phosphorylation was determined by mass spectroscopy. Using both methods, the degree of peptide phosphorylation was typically greater than 95% after incubation with the kinase. Negative control peptides were incubated under identical conditions to those for the phosphorylated peptides, but were incubated in the absence of ATP.

Fluorescence Changes Upon Cleavage

To initially test cleavage of the optical probes, fluorescence emission measurements were made in a cuvette, using a steady-state fluorimeter (SPEX). In the case of fluorescein/coumarin labeled peptides, emission spectra between 420 and 600 nm were obtained by excitation at 405 nm, (where coumarin absorbs maximally and there is little direct excitation of fluorescein). Typically the concentration of the optical probes was 100 nM, and the total reaction volume was 700 µL.

Figure 2:
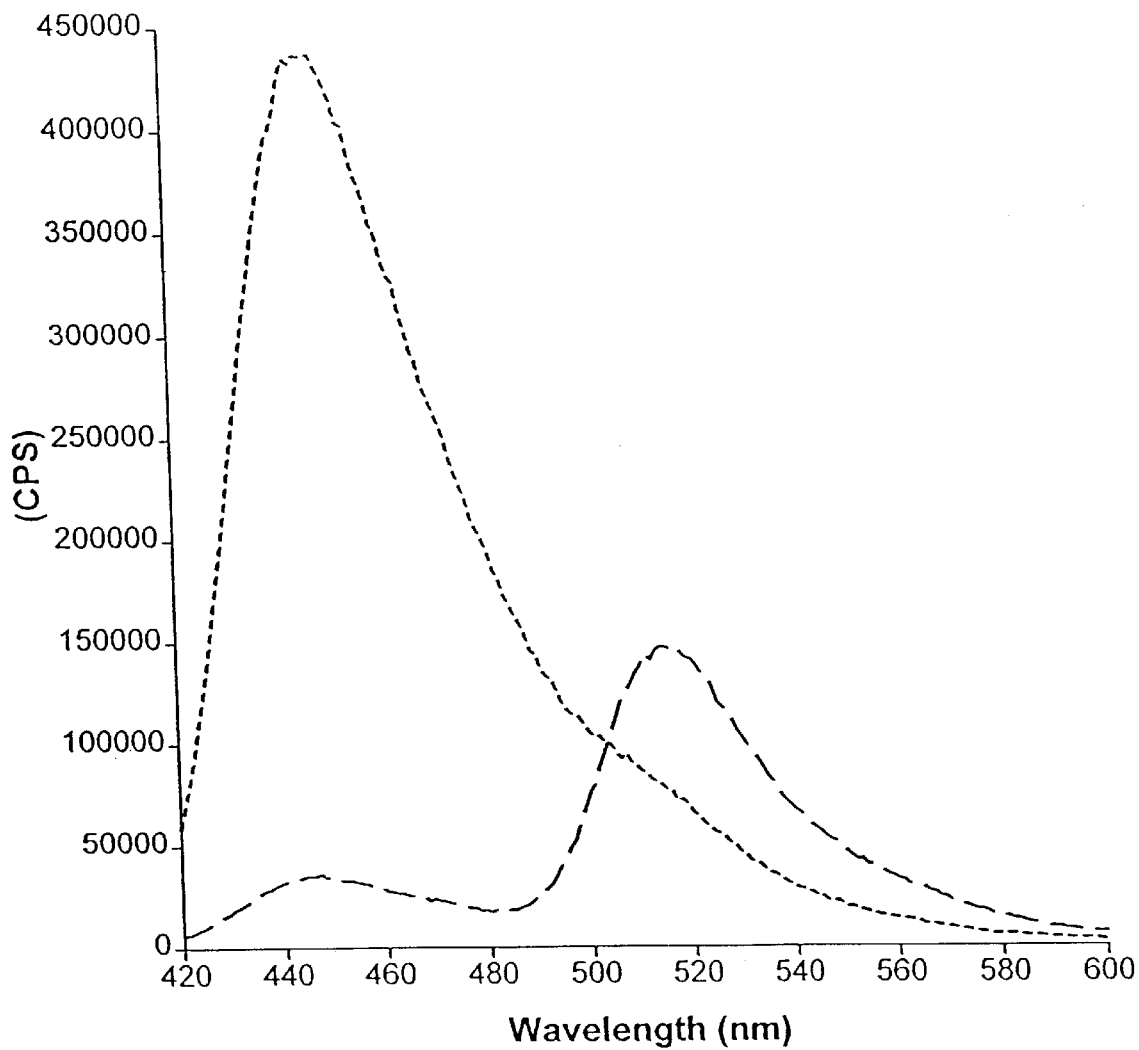
FIG. 2 Shows fluorescence emission spectra of cleaved and non-cleaved abl substrate peptides, (AEAIYAAPL, SEQ. ID. NO:4). Dotted lines represent the spectra of the cleaved optical probe, and dashed lines represent the non-cleaved probe.

FIG. 2 shows that cleavage of the non-phosphorylated optical probes by chymotrypsin results in a large increase in fluorescence emission at around 460 nm, and smaller decrease in emission at 530 nm that is caused by the loss of fluorescence resonance energy transfer (FRET) between the donor (coumarin) and acceptor (fluorescein). By comparison, the phosphorylated optical probe, is not degraded by chymotrypsin, and exhibits almost no change in emission characteristics at either wavelength upon incubation with the protease. The substantial 30-fold difference in emission ratios of phosphorylated (non-cleaved) substrate and non-phosphorylated (cleaved) substrate provides the basis for one aspect of the present invention. It should be further noted that since the emission spectra varies independently at two distinct wavelengths, it is possible to calculate an emission ratio, which has several significant advantages compared to single wavelength measurements. These include greater sensitivity and reproducibility in screening applications because the ratio is largely independent (within certain limits) of the absolute light intensity and optical probe concentration.

To confirm that the emission ratio is directly related to the degree of optical probe phosphorylation, mixtures of phosphorylated and non-phosphorylated samples of the abl substrate, (AEAIYAAPL, SEQ. ID. NO: 4) were mixed in defined amounts and diluted to 100 □L with 0.1×PBS and then added to a 96-well multiwell plate. Emission ratios (460/530) were acquired with a Cytofluor plate reader (Perspective Biosystems) using a 395 nm excitation filter [fall-width half-maximum (FWHM) of 25 nm] a 460 nm emission filter (FWHM=40 nm) and a 530 nm emission filter (FWHM=50 nm). Measurements were made before, and 1 minute after, addition of 0.04 nMol bovine alpha-chymotrypsin (Calbiochem, 230832, 1,018 USP units/mg), and the 460/530 emissions ratios calculated. The results, shown in Table 8, demonstrate a direct relationship between the degree of optical probe phosphorylation and the 460/530 emission ratio.

TABLE 8

| % of Phosphorylated Peptide | Best Fit | 460/530 Emission Ratio Actual Data |
|---|---|---|
| 0 | 0.904 | 0.904 |
| 10 | 2.118 | 2.086 |
| 20 | 3.331 | 3.256 |
| 30 | 4.545 | 4.193 |
| 40 | 5.758 | 5.440 |
| 50 | 6.972 | 6.498 |

TABLE 8-continued

| % of Phosphorylated Peptide | Best Fit | 460/530 Emission Ratio Actual Data |
|---|---|---|
| 60 | 8.186 | 7.919 |
| 70 | 9.399 | 9.332 |
| 80 | 10.613 | 10.598 |
| 90 | 11.826 | 11.865 |
| 100 | 13.040 | 13.044 |

Optimization of Protease Concentration

Figure 3:
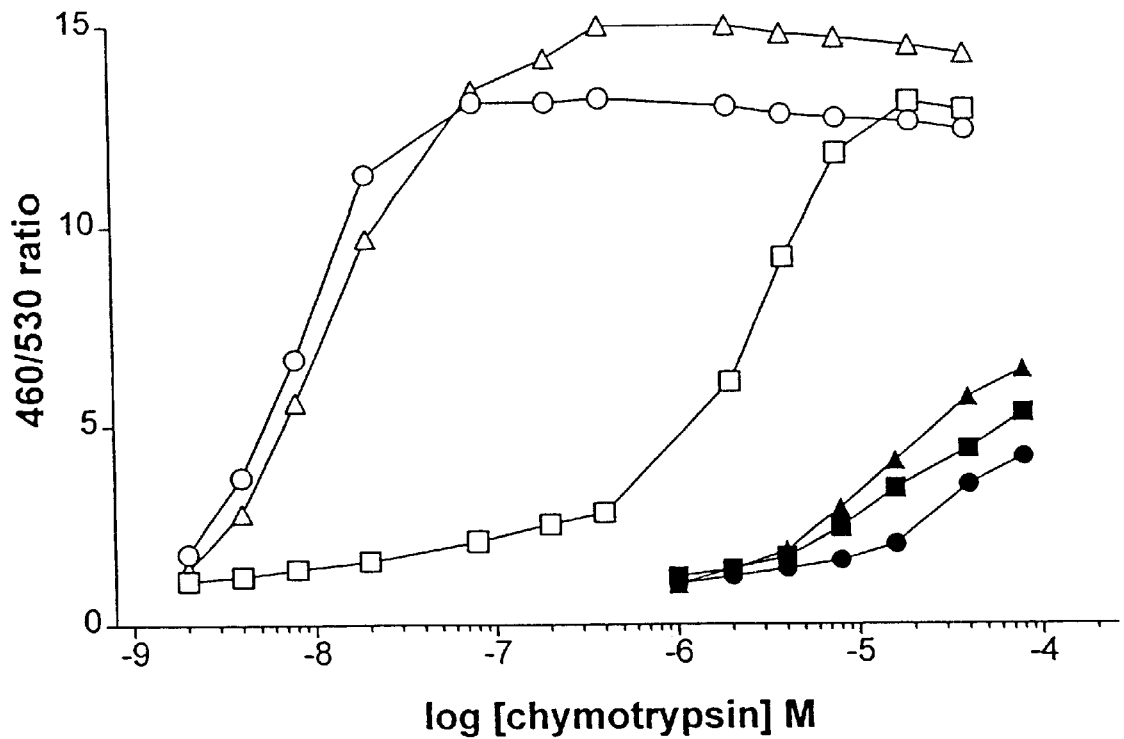
FIG. 3 Shows the dependency of 460/530 nm emission spectra ratios of certain optical probes (+/−kinase treatment) of the present invention upon incubation with increasing concentrations of a protease (chymotrypsin). Open symbols represent control samples, filled symbols represent phosphorylated samples, Squares represent the Src-1 substrate (GEEEIYGEIEK, SEQ. ID. NO: 3), triangles represent the Src-2 substrate (GEEEIYGVIEK, SEQ. ID. NO: 29) and circles represent the Abl substrate (AEAIYAAPL, SEQ. ID. NO: 4).

To determine the relative proteolytic sensitivity of the phosphorylated and non-phosphorylated optical probes, including the Src-1 substrate, (GEEEIYGEIEK, SEQ. ID. NO: 3), the Src-2 substrate, (GEEEIYGVIEK, SEQ. ID. NO: 29) and the abl-substrate, (AEAIYAAPL, SEQ. ID. NO: 4), samples of both were incubated with various concentrations of chymotrypsin, in 0.1×PBS. Fluorescence measurements were made on a 96-well plate reader as described previously. In FIG. 3, the open symbols represent the control, non-phosphorylated optical probe. In this case, cleavage of the optical probe, as indicated by the 460/530 emission ratio, is already significant at 10 nM chymotrypsin and reaches a maximum value of around 12, in the presence of 100 nM protease under these conditions. By comparison, the phosphorylated optical probe (filled symbols) does not begin to exhibit a comparable change in emission ratio until exposed to a 1000-fold higher concentration of protease (10 µM). These results demonstrate that maximal differences in emission ratio between phosphorylated and non-phosphorylated optical probe can occur, in this case, at protease concentrations between 0.1 to 1 µM chymotrypsin. Under these conditions, virtually all of the non-phosphorylated optical probe has been cleaved whereas virtually all of the phosphorylated optical probe is still intact. Optimal protease incubation conditions for other specific optical probes can be determined using similar procedures and protocols.

Example 2

Validation of Optical Probes for Screening for Protein Tyrosine Kinase Inhibitors To validate the invention in a high throughput screening format, optical probe-based assays were carried out in a 96-well plate reader using the abl substrate, (AEAIYAAPL, SEQ. ID. NO: 4). The results demonstrated highly reproducible and accurate results with the present invention. As shown in Table 9, the calculation of emission ratios significantly reduces the standard deviation and C.V. values compared to intensity measurements at either 460 or 530 nm. The reduction of errors is an important consideration in the design and analysis of screening systems, and particularly automated high throughput and ultra-high through screening systems.

TABLE 9

|  | Emission 460 nm | Emission 530 nm | Ratio |
|---|---|---|---|
| Mean | 1290 | 1922 | 0.67 |
| Standard Deviation | 3.7 | 4.8 | 0.01 |
| C.V. | 2.9% | 2.5% | 1.5% |

Analysis of the kinetics of phosphorylation of the optical probe revealed values for the apparent Km for the substrate of 40 μM, and an apparent Km for ATP of 8 μM. The turnover of the optical probe by v-Abl was 9.5 sec$^{-1}$, in agreement with published values for purified tyrosine kinases and optimal peptide substrates. For example, Seethala and Menzel., Anal Biochem. 253: 210–218 (1997); Songyang et al., Nature 373: 536–539 (1995).

Comparison to Other Methods of Screening.

To determine how the optical probe-based kinase assay compared to other screening methods, such as the direct measurement of $^{32}$P-incorporation into a peptide, a direct comparison of the two methods was completed. Samples of fluorescent substrate (2 μM) were phosphorylated with v-Abl kinase as described above in either the presence, or absence, of $_γ$-labeled $^{32}$P-ATP (0.5 μM or 10 μCi per 20 μl reaction.) In the case of the $^{32}$P-incorporation experiments, radioactive incorporation was determined by the binding of the optical probe to P81 filters as described previously (e.g., Seethala and Menzel, Anal. Biochem, 253:210–218, 1997). Abl peptide binding to P81 filters proved to be able to reliably capture a constant fraction of phosphorylated peptide. Radioactive incorporation into the optical probe was monitored using a TopCount liquid scintillation counter (Packard). Incubation of the optical probe with chymotrypsin (100 nM) and measurement of fluorescence emission ratios were as described in Example 1. Results from a typical experiment are shown in Table 10, and demonstrate that both methods of measuring tyrosine kinase activity give similar results and reliably indicate the level of substrate phosphorylation.

TABLE 10

| Concentration of Enzyme (ng/assay) | % Phosphorylation as Determined by Fluorescence | % Phosphorylation as Determined by $^{32}$P-Incorporation |
|---|---|---|
| 0 | 0.0 | 0.0 |
| 0.5 | 3.1 | 4.6 |
| 1.5 | 9.0 | 12.3 |
| 4.0 | 36.8 | 42.1 |
| 10.0 | 69.2 | 65.6 |
| 22.0 | 96.0 | 95.5 |
| 44.0 | 100.0 | 100.0 |

Characterization of a Protein Tyrosine Kinase Inhibitor in a Screening Assay

Figure 4:
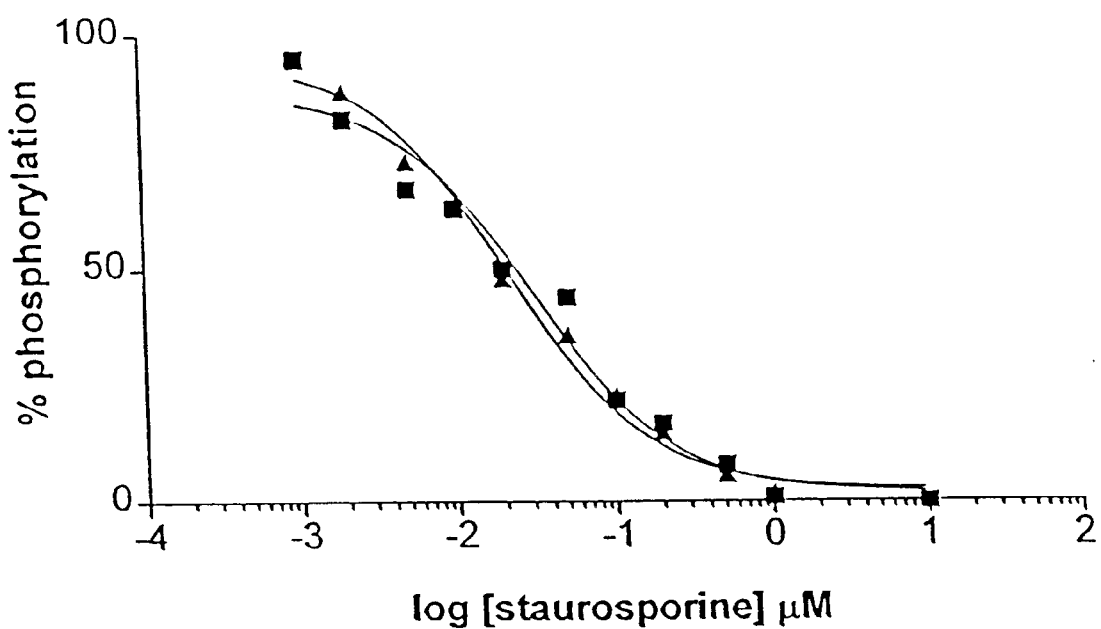
FIG. 4 Shows the comparison of fluorescent changes mediated by the phosphorylation and proteolysis of the abl substrate, (AEAIYAAPL, SEQ. ID. NO: 4) compared to $^{32}$P-incorporation for the detection of inhibitors of tyrosine kinase activity. Triangles represent optical probe measurements, squares represent $^{32}$P-incorporation measurements.

To demonstrate that the present invention can effectively identify inhibitors of tyrosine kinase activity, a direct comparison was completed to compare the effect of an inhibitor of tyrosine phosphorylation on either fluorescence changes after incubation with chymotrypsin, or $^{32}$P-incorporation (FIG. 4). The results demonstrated almost identical dose dependencies and inhibition curves for the inhibitor using either method of measuring tyrosine kinase activity. These experiments therefore demonstrate that the present invention provides for a sensitive and convenient system of measuring phosphorylation, and that the results obtained with the assay system are directly comparable to those obtained with by measuring $^{32}$P-incorporation.

Example 3

Measurement of Other Tyrosine Kinase Activities Using Optical Probes

Measurement of Src kinase activity

To measure Src kinase activity, two optical probes Src-1 (GEEEIYGEIEK, SEQ. ID. NO: 3) and Src-2 (GEEEIYGVIEK, SEQ. ID. NO: 29) were developed. In the case of the Src-1 kinase substrate, and as shown in Table 4, a second aromatic amino acid was changed to isoleucine in the optical probe. In the second substrate, Src-2, the negatively charged amino acid (Glu=E) in the P'$_2$ position with respect to the protease site, was changed to valine (Val=V) to enable more efficient cleavage of the non-phosphorylated optical probe by chymotrypsin. Src kinase (Upstate Biotechnology) reaction conditions were the same as described in Example 1, except 25 mM glycerol phosphate and 1 mM DTT were also added. Incubation of the optical probe with chymotrypsin (100 nM) and measurement of fluorescence emission ratios were as described in Example 1. The apparent $K_m$s for the two substrates, (determined by fluorescence measurements after protease incubation) with respect to the Src kinase were 11 μM and 19 μM respectively. Other optical probes, designed as described herein, can be generated to create specific optical probes for a range of tyrosine kinase activities that can subsequently be optimized using the methods described herein.

Example 4

Measurement of Protein Tyrosine Phosphatase Activities Using Optical Probes

To demonstrate that the present invention could also be used to determine protein tyrosine phosphatase activities, experiments were completed using phosphorylated optical probes incubated with protein tyrosine phosphatases. Optical probes were first phosphorylated to completion as described above, and samples of phosphorylated optical probe, at a final concentration of 500 nM, were incubated with various concentrations of protein tyrosine phosphatase-B (PTP-B) agarose (Upstate Biotechnology) for 20 minutes at 30 C in 0.1×PBS. At the required time interval, PTP-B-agarose was removed by a brief microfuige spin prior to transfer to 96-well Cytofluor plates for fluorescence measurements, after addition of chymotrypsin (100 nM), as described in Example 1.

Results from a typical experiment are shown in Table 11. In this experiment, the relative rates of dephosphorylation of the phosphorylated Src-2-specific substrate (SEQ. ID. NO: 29) and an abl-specific (SEQ. I.D. No. 4) substrate optical probes by the protein tyrosine phosphatase PTP-B were compared.

TABLE 11

| Log concentration of protein tyrosine phosphatase [PTP-B] | Fluorescence emission ratio of Src-2 (SEQ. ID. NO: 29) peptide after protease treatment | Fluorescence emission ratio of abl (SEQ. ID. NO: 4) peptide after protease treatment |
|---|---|---|
| −7.7 | 17.7 | n.d. |
| −8.7 | 17.6 | 17.7 |
| −9.7 | 15.8 | 17.8 |
| −10.7 | 5.40 | 16.6 |
| −11.7 | 1.99 | 8.60 |
| −12.7 | 1.75 | 5.70 |
| −13.7 | 1.62 | 5.30 |
| −14.7 | 1.60 | 5.30 |

In the case of the tyrosine phosphatase PTP-B, the Src-2 substrate is more readily de-phosphorylated than the abl substrate. Analysis of the enzyme kinetics, by virtue of a Michaelis-Menten plot, demonstrates that the apparent $K_m$ for the Src-2 optical probe is 1.3 μM and the $k_{cat}$ is 79 sec$^{-1}$. The $K_{cat}/K_m$ for this substrate is nearly $10^8$ M$^{-1}$sec$^{-1}$, indicating extremely efficient recognition of the phosphotyrosine containing optical probe. These experiments therefore demonstrate that the present invention provides for a sensitive and convenient system of measuring protein tyrosine phosphatase activity, and that the results obtained with the assay system are directly comparable to those obtained with other methods of measuring dephosphorylation. The relative broad substrate specificity of phosphotyrosine phosphatases (see, for example, Barford, et al. (1995) Nature Struct. Biol. 2: 1043–1053), suggest that the approach will be useful for measuring a wide range of protein tyrosine kinase activities.

Example 5

Figure 5:
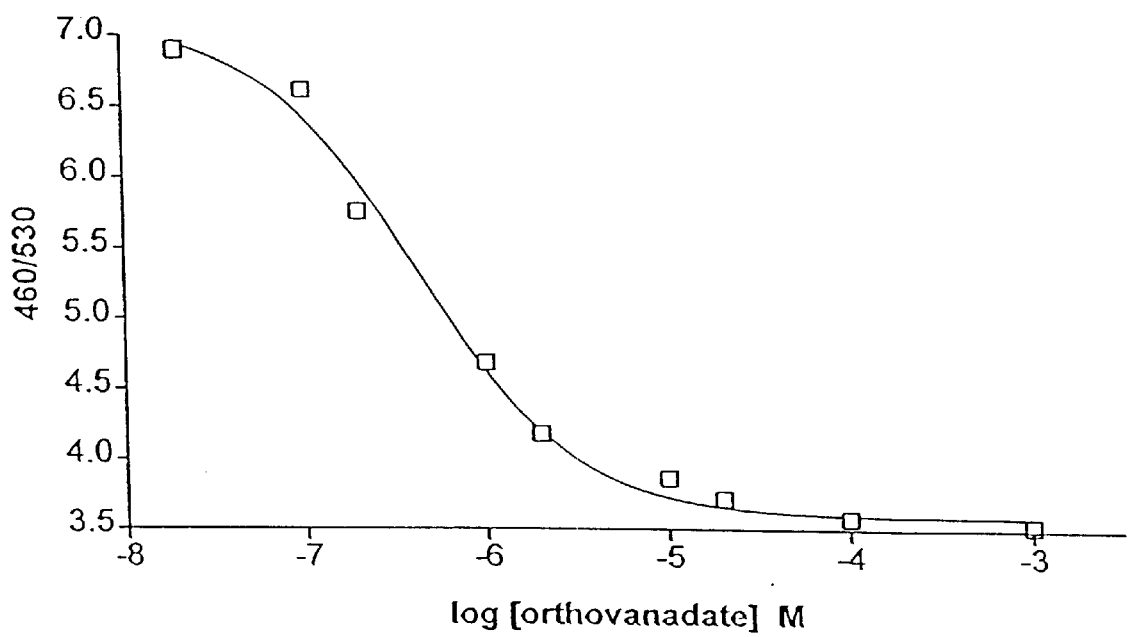
FIG. 5 Shows the detection of an inhibitor activity of protein tyrosine phosphatase activity by orthovanadate, using the phosphorylated Src-2 peptide (GEEEIYGVIEK, SEQ. ID. NO: 29) as substrate.

Validation of Optical Probes for Screening for Protein Tyrosine Phosphatase Inhibitors To demonstrate that the present invention can be used to identify and characterize protein tyrosine phosphatase inhibitors, experiments were carried in the absence, or presence of various concentrations of orthovanadate, a well characterized competitive inhibitor of tyrosine specific phosphatase activities. Ortho-vanadate competitively inhibited tyrosine phosphatase activity with an apparent $IC_{50}$ of 420 nM (FIG. 5) using the optical probes of the invention. This value is consistent with literature values of orthovanadate inhibition of PTP-B obtained by measuring $^{32}P$-labeling. This result demonstrates that the present invention can be used for the development of sensitive and selective screening assays for the identification and characterization of protein phosphatase activities.

Example 6

Measurement of Serine/Threonine Phosphorylation Using Optical Probes

Measurement of protein kinase A activity

To demonstrate that optical probe could be developed to measure serine or threonine kinases, peptides was designed that could be effectively recognized and phosphorylated by protein kinase A. In this case, the substrate was designed with a single aromatic amino acid (F) that was located immediately N-terminal to the phosphorylation site for protein kinase A, underlined in SEQ. ID. NO: 12, below, (the $P'_1$, position with respect to the protease cleavage site of chymotrypsin). This results in a modulation of the rate of optical probe cleavage by chymotrypsin after phosphorylation.

The peptide (RRRKFSLRRKA, SEQ. ID. NO: 12) was labeled with fluorescein isothiocyanate at the N-termninus and 7-hydroxycoumarin-3-carboxamide at the C-terminus as described above. To determine the relative proteolytic activity of the phosphorylated and non-phosphorylated optical probes, samples of both were prepared. To do this, 10 microM of the substrate, in a total volume of 10 μL, was phosphorylated to completion by incubation with excess protein kinase A for one hour at 30° C. in a buffer consisting of 50 mM TRIS-CL, pH 7.5, 10 mM $MgCl_2$, and 200 μM ATP. Mock kinase reactions with no ATP were used to create non-phosphorylated, control samples. In both cases, the samples were diluted 10 fold with buffer containing 50 mM HEPES, pH 7.5, 10 mM $CaCl_2$ and 0.01% Brij-35, and incubated with 0.8 nM chymotrypsin. Fluorescence emission ratios were monitored for one hour and are shown in Table 12.

TABLE 12

| Time of Cleavage (minutes) | Non-phosphorylated Optical probe | Phosphorylated Optical probe | Fold Difference in Ratios |
| --- | --- | --- | --- |
| 0  | 0.34 0.01  | 0.33 0.01 | 1.0 |
| 10 | 3.15 0.06  | 0.54 0.01 | 5.8 |
| 20 | 6.71 0.29  | 0.78 0.01 | 8.6 |
| 30 | 9.86 0.43  | 1.02 0.02 | 9.7 |
| 40 | 12.00 0.4  | 1.27 0.03 | 9.5 |
| 50 | 13.34 0.40 | 1.53 0.03 | 8.7 |
| 60 | 14.02 0.27 | 1.78 0.03 | 7.9 |

The maximum fold difference in 460/530 ratio was about 9.7 after 30 minutes of treatment with chymotrypsin. This ratio change therefore provides a robust and sensitive measure of protein phosphorylation that by virtue of its high signal to noise ratio is well suited for high throughput screening applications.

Example 7

Vaidation of Optical Probes for Screening far Serine/Threonine Kinase Inhibitors To demonstrate that the present invention could be used to identify and characterize serine/threonine kinase hinhibitors, experiments were carried out with a number of previously characterized inhibitors of serine /threonine kinase activity. In the case of the ATP-competitive inhibitors staurosporin and H-89, inhibitor at a final concentration of 10 μM was preincubated with protein kinase A and the fluorescent substrate (SEQ. ID. NO: 28) in 50 mM TRIS-Cl, pH 7.5, 10 MM $MgCl_2$, and the reactions were initiated by the addition of ATP (10 μM). For the substrate competitive inhibitor PKI, inhibitor (2.8 μM) was pre-incubated with enzyme before the addition of optical probe and ATP (100 μM) in the buffer described above. After one hour incubation at 30 C, chymotrypsin to a final concentration of 0.8 nM was added and the 460/530 ratio was determined after one hour, as described above (Example 6). The results showed almost complete inhibition of protein kinase A activity at the concentrations of inhibitor tested (Table 13A and 13B).

TABLE 13A

| Negative Control (No Active Kinase) 460/530 Emission Ratio | Positive Control (Active Kinase) 460/530 Emission Ratio | Kinase + the inhibitor Staurosporin (10 μM) 460/530 Emission Ratio | Kinase + the inhibitor H-89 (10 μM) 460/530 Emission Ratio |
| --- | --- | --- | --- |
| 14.02 0.27 | 1.78 0.03 | 13.92 0.07 | 13.29 0.14 |

TABLE 13B

| Negative Control (No Active Kinase) 460/530 Emission Ratio | Positive Control (Active Kinase) 460/530 Emission Ratio | Kinase + the inhibitor PKI (2.8 μM) 460/530 Emission Ratio |
|---|---|---|
| 11.67 0.48 | 2.11 0.19 | 1171 0.15 |

Validation of the Use of Optical Probes for High Throughput Screening

Figure 6:
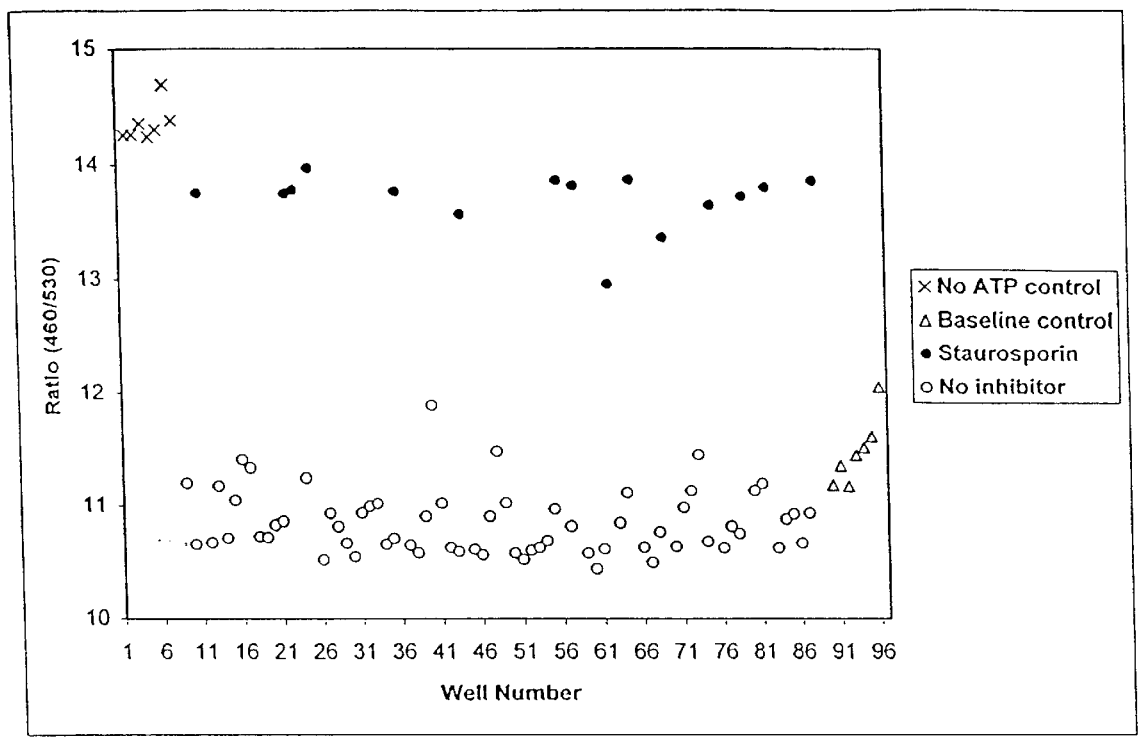
FIG. 6 Shows a mock high throughput screening validation to verify that the present invention can be used to identify inhibitors of serine/threonine kinase activity. The reactions were performed with protein kinase A, and the fluorescent substrate RRRFSRRRR (SEQ. ID. NO: 28).

To demonstrate that the present invention could reproducibly detect inhibitors in a high throughput type-screening assay, a screen was performed in a 96-well plate. The experiment was set up with randomly spiked wells containing a known protein kinase A inhibitor, staurosporin, under conditions where approximately 20% of the substrate was converted to phosphorylated product. The 96-well plate was set up with appropriate no-ATP and no-inhibitor controls. Fifteen wells were chosen at random and received 5 μL of 360 nM staurosporin (in 3% DMSO). The final concentration of staurosporin in the five spiked wells was 60 nM, equal to the $IC_{80}$ determined empirically. All other wells (including the no inhibitor wells) received 5 μL of 3% DMSO. All wells (except blanks) then received 10 μL of kinase reaction mix which included the optical probe (final concentration in the kinase reaction was 3.3 μM), buffer, and protein kinase A. After a 5 min pre-incubation, kinase reactions were started by the addition of 15 μL of 20 μM ATP, and incubated for 15 minutes at 30 C. Final kinase reaction concentrations were: 3.3 μM fluorescent substrate (SEQ. ID. NO: 28), 60 nM staurosporin, 0.004 units protein kinase A, 10 μM ATP, 10 mM $MgCl_2$. Kinase reactions were terminated by the addition of 30 μL of a buffer containing 50 mM HEPES, pH 7.4, 0.01% Brij-35, and 20 mM EDTA. Initial 460/530 ratios were obtained, and then the chymotrypsin reaction was started by the addition of 40 μL of a buffer containing 50 mM HEPES, pH 7.4, 0.01% Brij-35, and 2 nM chymotrypsin (50 ng/ml). Final chymotrypsin concentration in the reaction was 0.8 nM (20 ng/ml). 460/530 emission ratios were obtained after 30 minutes. In this assay format, all wells spiked with staurosporin were correctly assigned as positive hits for kinase inhibition (FIG. 6; filled in dots). Furthermore, in those wells, kinase activity was inhibited by about 80% when compared to the no ATP (negative) controls. The assay was highly reproducible, exhibiting a low coefficient of variance (Table 14).

TABLE 14

| Samples | Coefficient of Variance |
|---|---|
| No ATP (n = 7) | 1.6% |
| Control Kinase (n = 7) | 2.6% |
| Kinase + Inhibitor (n = 15) | 1.8% |
| Kinase, no Inhibitor (n = 65) | 2.6% |

Coefficient of Variance (in %) = 100 × (Standard Deviation/Mean)
N = number of wells Example 8

Measurement of Other Serine Threonine Kinase Activities

Measurement of Casein Kinase 1 Activity

To measure casein kinase 1 activity, an optical probe was designed as described above. In this case, the kinase substrate was designed so that the point of phosphorylation was located at the $P'_2$ position (underlined in SEQ. I.D. NO: 17 below) with respect to the scissile bond cleaved by chymotrypsin, which enables the creation of a recognition motif suitable for casein kinase 1. A substrate peptide (GDQDYLSLDK, SEQ. ID. NO: 17) was synthesized and labeled with fluorescein isothiocyanate at the N-terminus and 7-hydroxycoumarin-3-carboxamide at the C-terminus as described in Example 1.

Samples of phosphorylated and non-phosphorylated optical probes were prepared and tested as described in Example 1. In this case, complete phosphorylation of the optical probe (1 μM) was obtained after room temperature incubation for 15 to 30 minutes in the presence of 500 Units of casein kinase 1 (New England BioLabs) in 50 mM Tris-Cl, pH 7.5, 10 mM $MgCl_2$, 5 mM DTT, and 200 μM ATP.

To determine the relative proteolytic sensitivity of phosphorylated and non-phosphorylated optical probes, samples of both were incubated with various concentrations of chymotrypsin and the cleavage monitored by measuring the 460/530 emission ratio as described in Example 1. The results, shown in Table 15, demonstrate that the non-phosphorylated optical probe is significantly more susceptible to proteolytic cleavage at low concentrations of chymotrypsin than the phosphorylated optical probe.

TABLE 15

| Concentration of Chymotrypsin (μM) | Negative Control (No Active Kinase) 460/530 Emission Ratio | Positive Control (Active Kinase Only) 460/530 Emission Ratio | Fold difference in ratios |
|---|---|---|---|
| 0.04 | 3.0 | 1.2 | 2.5 |
| 0.1 | 6.6 | 1.4 | 4.7 |
| 0.2 | 10.9 | 1.7 | 6.4 |
| 0.3 | 12.3 | 1.9 | 6.5 |
| 0.4 | 14.3 | 2.3 | 6.2 |
| 1.0 | 15.4 | 3.8 | 4.1 |
| 2.0 | 15.6 | 6.0 | 2.6 |

In this experiment, the maximum fold difference in 460/530 emission ratios of non-phosphorylated substrate versus phosphorylated substrate occurred at a chymotrypsin concentration of about 0.3 μM chymotrypsin. At this concentration the difference in emission ratios of phosphorylated and non-phosphorylated fluorescence samples Was greater than 6 fold, demonstrating that the present invention provides for highly sensitive methods of measuring this class of serine/threonine kinase activities in a screening format.

Measurement of ERK Kinase Activity

To demonstrate that the present invention could also be used to detect the activity of a proline-directed serine/threonine kinase, an optical probe (VAPFSPGGRAK, SEQ. ID. NO: 27) was designed as a substrate for extracellular signal-regulated kinase (ERK) containing the serine phosphorylated, (shown underlined in SEQ. ID. NO: 27) in the $P_1'$ position relative to the chymotrypsin cleavage site (F). This substrate (100 μM) was phosphorylated by incubation at 30 C for 3 hours in a 100 μL reaction containing 500 ng ERK (Biomol) and 500 μM ATP in a buffer consisting of 50 mM Tris-Cl, pH 7.5, 10 mM $MgCl_2$, 1 mM EGTA, 2 mM DTT, and 0.01% Brij-35. To test the proteolytic sensitivity of phosphorylated and non-phosphorylated samples, 2 μL of the mock (no kinase) or kinase reaction was diluted to 100 μL in a buffer containing 50 mM HEPES, pH 7.5, 10 mM $CaCl_2$, and 0.01% Brij-35, and incubated with chymotrypsin at a concentration of 4 nM. Cleavage reactions were monitored on the Cytofluor for 1 hr. The results demonstrate that phosphorylated optical probe was less sensitive to chymotrypsin than the non-phosphorylated peptide (Table 16). The maximum fold difference in 460/530 ratio was about 15.2 and occurred after 30 minutes of cleavage. These data demonstrate that the present invention can be used to monitor activity of a proline-directed kinase.

Example 9

Measurement of Serine/Threonine Phosphatase Activities

Protein Phosphatase I Activity

To determine if the optical probes could be used to detect serine/threonine phosphatase activities, samples of the casein kinase 1 specific phosphorylated optical probes were prepared and treated with various serine/threonine protein phosphatases. To do this, the casein kinase 1 optical probe (GDQDYLSLDK, SEQ. ID. NO: 17) (100 μM) was phosphorylated to completion with CKI (2000 units) in a 100 μL reaction containing 200 μM ATP for 5 hours at 30° C. A mock kinase reaction was performed which contained no ATP for preparation of control, non-phosphorylated optical probes. The resistance of the phosphorylated optical probe to chymotrypsin cleavage (data not shown) confirmed complete phosphorylation of the CKI-treated optical probe. Phosphorylated and non-phosphorylated samples of the optical probe (2 μM) were incubated in a 50 μL volume with or without 1 unit of the serine/threonine phosphatase protein phosphatase I (PPI) for 2 hours at 30° C. in a buffer consisting of 50 mM Tris-Cl, pH 7.0, 0.1 mM EDTA, 5 mM DTT, 0.01% Brij-35, and 1 mM $MnCl_2$. The reactions were diluted to 100 μL with 50 mM HEPES, pH 7.5, incubated with chymotrypsin (0.2 μM) for 1 hour at room temperature, and fluorescence values were measured on the Cytofluor as described above. Before chymotrypsin addition all reactions had similar 460/530 ratios of about 1.2.

TABLE 16

| Time of cleavage (min) | Negative Control (No Active Kinase) 460/530 Emission Ratio | Positive Control (Active Kinase) 460/530 Emission Ratio | Fold difference in ratios |
| --- | --- | --- | --- |
| 0 | 0.28 | 0.33 | 0.85 |
| 10 | 4.17 | 0.44 | 9.45 |
| 20 | 7.56 | 0.56 | 13.55 |
| 30 | 10.03 | 0.66 | 15.16 |
| 40 | 11.71 | 0.78 | 14.99 |
| 50 | 12.73 | 0.89 | 14.34 |
| 60 | 13.40 | 1.00 | 13.36 |

Measurement of Protein Kinase C Activity

To measure protein kinase C activity using the optical probes of the present invention, a peptide (RRRKFSLRRKA, SEQ. ID. NO: 12) was designed in which phosphorylation by protein kinase C occurred at the $P'_1$ position (underlined in SEQ. ID. NO: 12) with respect to the scissile bond cleaved by chymotrypsin. This enabled an optimal protein kinase C recognition motif to placed within the optical probe sequence, and to create a site of phosphorylation that modulated the proteolytic sensitivity of the substrate towards chymotrypsin. Analysis of phosphorylated and non-phosphorylated samples of the optical probe revealed that phosphorylation by protein kinase C significantly modulated the proteolytic susceptibility of the substrate. These results demonstrate that the present invention can be used to develop optical probes that can measure protein kinase C activity.

TABLE 17

| | Non-phosphorylated Control | Phosphorylated Control | Phosphorylated Control + Phosphatase (PP1) |
| --- | --- | --- | --- |
| 460/530 Emission Ratio After Chymotrypsin | 9.8 | 2.0 | 10.0 |

After chymotrypsin addition (Table 17) the 460/530 ratio of the non-phosphorylated optical probe was 9.8, whereas the 460/530 ratio of the phosphorylated optical probe was 2.0. However, when the phosphorylated optical probe was first treated with PP1 and then with chymotrypsin, the 460/530 ratio was 10.0, indicating that PP1 dephosphorylated nearly all of the optical probe.

Protein Phosphatase 2A Activity

The optical probes were also evaluated to determine if they could be used to measure protein phosphatase 2A (PP2A) activity. Phosphorylated and non-phosphorylated samples of the CKI optical probes (SEQ. ID. NO: 23) were prepared and incubated with 0.03 units of PP2A as described above, except $MnCl_2$ was not included. After dilution and addition of chymotrypsin as described above, fluorescence values were measured using a 96 well plate reader (Cytofluor). After a 1.5 hour chymotrypsin incubation, the 460/530 emission ratio of the phosphorylated optical probe was 1.8±0.2 (Table 18).

TABLE 18

|  | Non-phosphorylated Control | Phosphorylated Control | Phosphorylated Control + Phosphatase (PP2A) |
|---|---|---|---|
| 460/530 Emission ratio After Chymotrypsin | 11.0 ± 0.1 | 1.8 ± 0.2 | 8.8 ± 0.1 |

However, when the phosphorylated optical probe was first incubated with PP2A followed by chymotrypsin, the 460/530 ratio was 8.8±0.1. This value is approximately 80% of that obtained when the non-phosphorylated optical probe was treated with chymotrypsin (11.0±0.1). Thus, a majority of the phosphorylated optical probe was dephosphorylated under the conditions used. Taken together, these data indicate that the present invention can also be used as an assay for the activity of the serine/threonine phosphatase PP2A.

Example 10

Validation of Optical Probes for Screening for Serine or Threonine Protein Phosphatase Inhibitors Identification of Protein Phosphatase 1 Inhibitors To determine if the optical probe protein phosphatase assay could detect inhibitors of PP1, the phosphatase assay was performed in the presence or absence of 1 $\mu$M microcystin-LR, a potent inhibitor of PP1. Phosphatase assays were set up as described above except the phosphatase was allowed to pre-incubate with microcystin-LR for 10 minutes before the addition of phosphorylated or non-phosphorylated optical probes (SEQ. ID. NO: 23). PP1 reactions were incubated at 30 C for 1 hour and then diluted to 100 $\mu$L in 50 mM HEPES, pH 7.5 followed by the addition of chymotrypsin to 0.2 $\mu$M. Fluorescence values were measured on the Cytofluor after a 2 hour incubation at room temperature as described above. After treatment of the phosphorylated optical probe with PP1 followed by chymotrypsin, the 460/530 ratio was 13.2±0.2. This value was identical to that of the non-phosphorylated optical probe (13.2±0.1) indicating that PP1 completely dephosphorylated the CKI-treated optical probe in this experiment (Table 19). However, in the presence of 1 $\mu$M microcystin-LR, PP1 activity was almost completely inhibited as demonstrated by the 460/530 ratio, which was 2.8±0.1. Control samples, in which non-phosphorylated optical probe was treated with microcystin-LR gave a final 460/530 ratio of 13.3±0.2, demonstrating that microcystin-LR did not inhibit chymotrypsin cleavage. Thus, the present invention could be used to detect inhibitors of PP1 activity.

TABLE 19

|  | Non-phosphorylate Optical probe + PP1 | Phosphorylated Optical probe + PP1 | Non-phosphorylated Optical probe + PP1 + microcystin-LR | Phosphorylated Optical probe + PP1 + microcystin-LR |
|---|---|---|---|---|
| After Chymotrypsin | 13.2 ± 0.1 | 13.2 ± 0.2 | 13.3 ± 0.2 | 2.8 ± 0.1 |

Identification of Protein Phosphatase 2A Inhibitors

To determine if the optical probe phosphatase assay could detect inhibitors of PP2A, the phosphatase assay was performed in the presence or absence of 100 nM microcystin-LR. PP2A assays were set up as described above, and were incubated at 30 C for 2 hours. Reactions were diluted to 100 $\mu$L with 50 mM HEPES, pH 7.5 followed by the addition of chymotrypsin to 0.2 $\mu$M. Fluorescence values were measured on the Cytofluor after a 1.5 hour incubation at room temperature. As described above, treatment of the phosphorylated optical probe (SEQ. ID. NO: 23) with PP2A followed by chymotrypsin gave a final 460/530 ratio of 8.8±0.1. However, in the presence of 100 nM microcystin-LR, PP2A activity was completely inhibited as demonstrated by the 460/530 ratio of 1.9±0.1 (Table 20). Control samples in which non-phosphorylated optical probe was treated with microcystin-LR and chymotrypsin gave a final 460/530 ratio of 11.1±0.2, demonstrating that microcystin-LR did not inhibit chymotrypsin cleavage. Thus, the optical probe based phosphatase assay can detect inhibitors of PP2A activity.

TABLE 20

|  | Non-phosphorylate Optical probe + PP2A | Phosphorylated Optical probe + PP2A | Non-phosphorylated Optical probe + PP2A + microcystin-LR | Phosphorylated Optical probe + PP2A + microcystin-LR |
|---|---|---|---|---|
| Before Chymotrypsin | 1.4 ± 0.0 | 1.3 ± 0.0 | 1.4 ± 0.1 | 1.4 ± 0.1 |
| After Chymotrypsin | 11.1 ± 0.1 | 8.8 ± 0.1 | 11.1 ± 0.2 | 1.9 ± 0.1 |

Example 11

Use of Other Proteases to Measure Kinase Activity
Measurement of ERK Kinase Activity To determine how phosphorylation on serine in the optical probe (SEQ. ID. NO: 24) effected the rate of caspase-3 cleavage, samples of phosphorylated and control (non-phosphorylated) optical probes were treated with the protease caspase-3. Phosphorylated samples of the optical probe (70 pmol) were prepared by 8 hour to overnight incubation with ERK2 kinase (Biomol). Reactions were typically performed in 10 µl using 200–500 µM ATP and 50–200 ng ERK2 in a buffer consisting of 50 mM HEPES, pH 7.5, 10 mM $MgCl_2$, 1 mM EGTA, and 1 mM DTT at 30° C. Mock kinase reactions were performed for preparation of control (non-phosphorylated) optical probe as above, except ATP was omitted. To monitor cleavage of the optical probes by caspase-3, 10 µL volumes of phosphorylated and control (non-phosphorylated) samples of the optical probe were placed in individual wells of a 96-well multiwell plate. Caspase-3 cleavage reactions were carried out in these samples after dilution to 100 µL in a buffer consisting of 100 mM HEPES, pH 7.5, 5 mM DTT, 0.5 mM EDTA, 20% glycerol, 0.01% Brij-35, and 50–100 ng caspase-3 (Upstate Biotechnology), and incubated at room temperature. Emission readings were taken at 5 minute intervals during the course of the caspase-3 incubation using a Cytofluor plate reader as described in Example 1.

Figure 7:
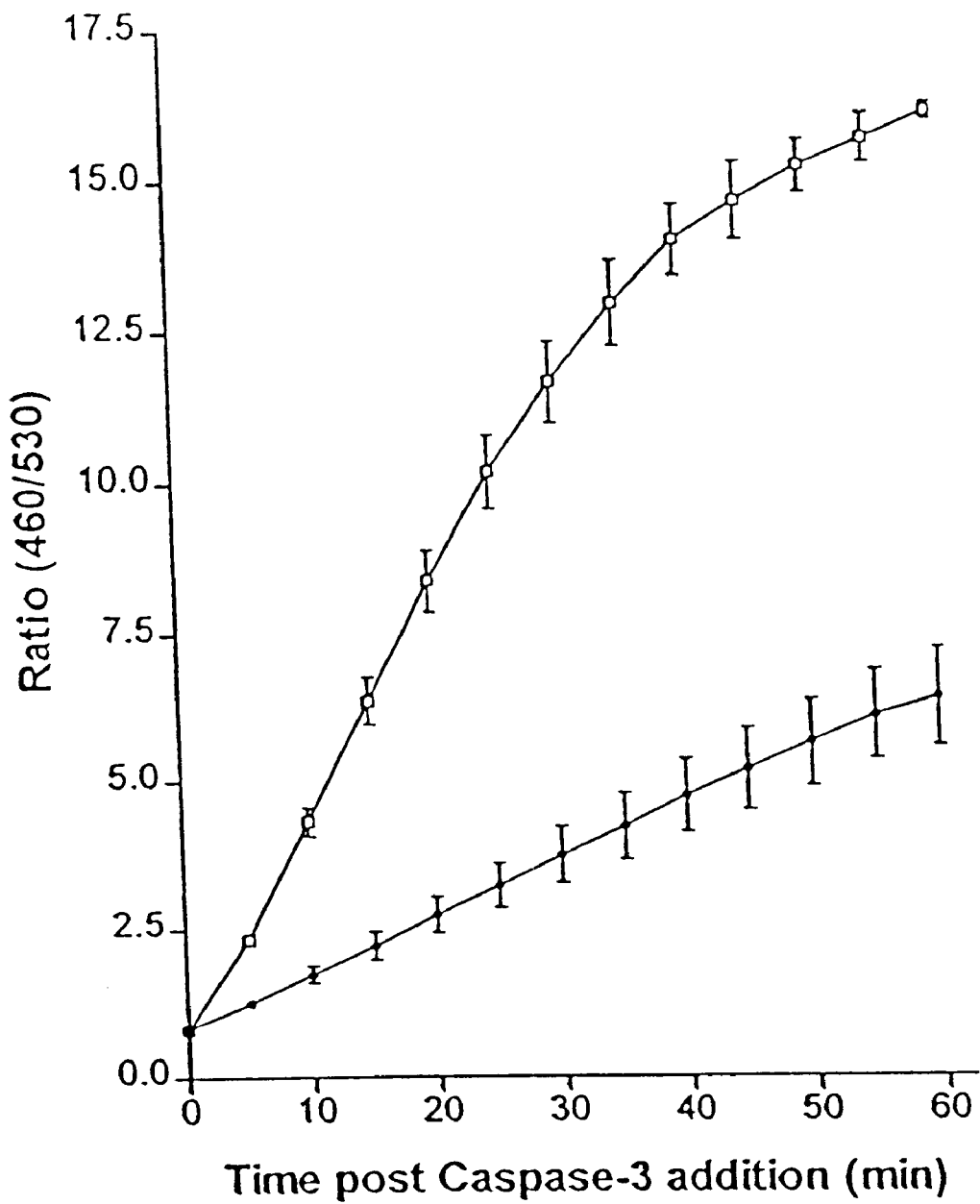
FIG. 7 Shows the caspase-3 mediated cleavage of phosphorylated (filled symbols) and non-phosphorylated (open symbols) ERK kinase specific optical probes of the present invention.

As shown in FIG. 7, the 460/530 emission ratio, which as described above, (Example 1) indicates increased cleavage of the optical probe, changes more rapidly for the control (non-phosphorylated) optical probe than it does for the phosphorylated substrate. These results demonstrate that phosphorylation of the optical probe by a serine /threonine directed protein kinase results in a modulation of the rate of cleavage of that substrate by, caspase-3. The maximal differences in fluorescence emission ratio occurred in this case after 30 minutes exposure to caspase-3, and resulted in over a three fold difference in emission ratio of phosphorylated and non-phosphorylated optical probes.

Measurement of Serine or Threonine Kinase Inhibitors

To confirm that the assay method could be used to detect inhibitors of ERK kinase activity, the effect of roscovitine (a known ERK kinase inhibitor) were examined using the present invention. To do this, ERK kinase (50 ng) was pre-incubated with the indicated amounts of roscovitine (Calbiochem), in the presence of 100 µM ATP. After 10 minutes optical probes (to a final concentration of 0.7 µM) were added and the incubations continued for an additional 2 h at 30° C. After incubation, reactions were diluted to 100 µl and fluorescence measurements made as described above in Example 6.

Figure 8:
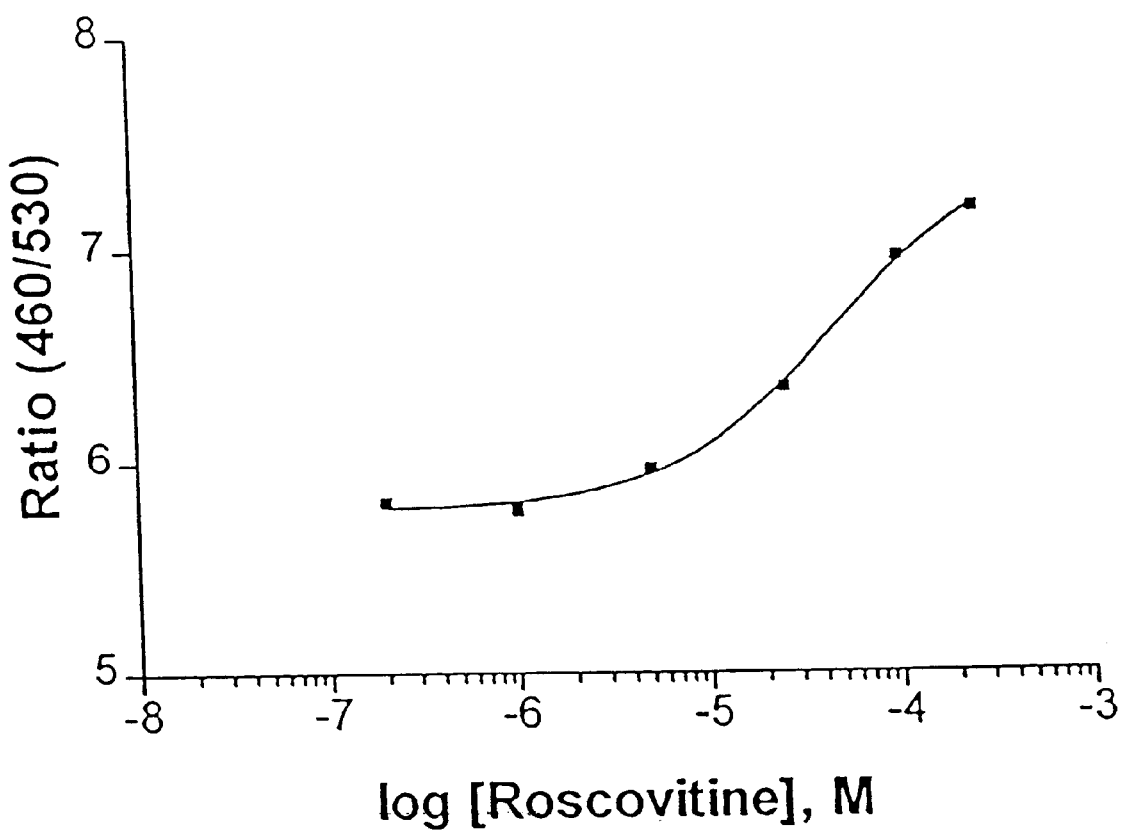
FIG. 8 Shows the inhibition of ERK kinase activity by roscovitine using certain optical probes of the present invention.

The results show FIG. 8, that the assay was able to detect the presence of the kinase inhibitor. The calculated $IC_{50}$ for roscovitine using the optical probe based assay was 45 µM. These experiments therefore demonstrate that the present invention provides for a sensitive and convenient system of measuring Erk serine/threonine kinase inhibitor activity.

The present invention provides novel optical probes and methods for their use. While specific examples have been provided, the above description is illustrative and not restrictive. Many variations of the invention will become apparent to those skilled in the art upon review of this specification. The scope of the invention should, therefore, be determined not with reference to the above description, but instead should be determined with reference to the appended claims along with their full scope of equivalents.

All publications and patent documents cited in this application are incorporated by reference in their entirety for all purposes to the same extent as if each individual publication or patent document were so individually denoted.

SEQUENCE I.D. NO: LISTING

SEQ. ID. NO: 1 MEEIYGELS
SEQ. ID. NO: 2 DEEIYESLE
SEQ. ID. NO: 3 GEEEIYGEIEK
SEQ. ID. NO: 4 AEAIYAAPL
SEQ. ID. NO: 5 EPIYMLSL
SEQ. ID. NO: 6 EEEYMMMM
SEQ. ID. NO: 7 EEEEYVVI
SEQ. ID. NO: 8 EEEEYVLLV
SEQ. ID. NO: 9 AEEEYFVLM
SEQ. ID. NO: 10 RRRFSIIII
SEQ. ID. NO: 11 RRFRSIIH
SEQ. ID. NO: 12 RRRKFSLRRKA
SEQ. ID. NO: 13 LRRRFSASNL
SEQ. ID. NO: 14 KRQFSIDLK
SEQ. ID. NO: 15 KRFQSIDLK
SEQ. ID. NO: 16 GDQDTYSLLDK
SEQ. ID. NO: 17 GDQDYLSLDK
SEQ. ID. NO: 18 EDEFSEDEE
SEQ. ID. NO: 19 EDFESEDEE
SEQ. ID. NO: 20 HHHFSPRKR
SEQ. ID. NO: 21 HHFRSPRKR
SEQ. ID. NO: 22 HHHFSPRRR
SEQ. ID. NO: 23 HHFKSPRRR
SEQ. ID. NO: 24 RVDEPFSPGEK
SEQ. ID. NO: 25 PRPFSVPP
SEQ. ID. NO: 26 RRRFSLRRI
SEQ. ID. NO: 27 RRFGSLRRI
SEQ. ID. NO: 28 RRRFSRRRR
SEQ. ID. NO: 29 RRFHSRRRR

We claim:

1. A method for measuring a post-translational modification activity, comprising:
   a) contacting a sample with an engineered optical probe, said engineered optical probe comprising:
      a polypeptide comprising a first probe moiety,
         wherein said polypeptide comprises a recognition motif for a post-translational type modification within said polypeptide, and a protease site located within said polypeptide; and
         wherein post-translational type modification of said recognition motif modulates the rate of cleavage of said polypeptide by a protease with specificity for said protease site,
   b) contacting said sample and said engineered optical probe with a protease with specificity for said protease site, and
   c) detecting a change in at least one optical property of said engineered optical probe.

2. The method of claim 1, wherein said polypeptide does not exceed 15 amino acids in length.

3. The method of claim 1, wherein said polypeptide does not exceed 50 amino acids in length.

4. The method of claim 1, wherein said optical property comprises a fluorescent property.

5. The method of claim 4 wherein said fluorescence property is fluorescence anisotropy.

6. The method of claim 5, wherein said polypeptide is attached to a solid matrix.

7. The method of claim 1, further comprising a fluorescent quencher attached to said polypeptide, wherein said recognition motif and said protease site are located between said first probe moiety and said fluorescent quencher.

8. The method of claim 1, wherein said optical property is fluorescence emission.

9. The method of claim 8, wherein said polypeptide is attached to a bead.

10. The method of claim 1, further comprising a second probe moiety attached to said polypeptide, wherein said recognition motif and said protease site are located between said first probe moiety and said second probe moiety.

11. The method of claim 10, wherein said optical property is fluorescence resonance energy transfer.

12. The method of claim 8, wherein said optical property is bioluminescence/emission.

13. The method of claim 8, wherein said protease is one of the following caspase 3, cathepsin G, chymotrypsin, elastase, endoproteinase Asp-N or endoproteinase Glu-N.

14. The method of claim 8, wherein said post-translational type activity is protein tyrosine kinase activity or protein tyrosine phosphatase activity.

15. The method of claim 8, wherein said post-translational type activity is protein serine or threonine kinase activity or protein serine or threonine phosphatase activity.

16. The method of claim 1, wherein said first probe moiety comprises a fluorophore selected from the group consisting of fluorescein-5-isothiocyanate, dichlorotriazinylaminofluorescein, tetramethylrhodamine-5 or 6-isothiocyanate, 1,3-bis-(2-dialkylamino-5-thienyl)-substituted squarines, carboxyfluoroscein; 5 or 6-carboxytetramethylrhodamine; and 7-amino-4-methylcoumarin-3-acetic acid.

17. The method of claim 1, wherein said first probe moiety comprises coumarin.

18. The method of claim 17, wherein said first probe moiety comprises 7-hydroxy coumarin.

19. The method of claim 1, wherein said first probe moiety comprises rhodamine.

20. The method of claim 19, wherein said first probe moiety comprises rhodamine B.

21. The method of claim 1, wherein said first probe moiety comprises fluorescein.

22. The method of claim 21, wherein said first probe moiety comprises fluorescein-5-isothiocyanate.

23. The method of claim 11, wherein said first probe moiety comprises a lanthanide complex.

24. The method of claim 11, wherein said first probe moiety, or said second probe moiety comprises a fluorophore selected from the group consisting of fluorescein-5-isothiocyanate, dichlorotriazinylaminofluorescein, tetramethylrhodamine-5 or 6-isothiocyanate, 1,3-bis-(2-dialkylamino-5-thienyl)-substituted squarines, carboxyfluoroscein; 5 or 6-carboxytetramethylrhodamine; and 7-amino-4-methylcoumarin-3-acetic acid.

25. The method of claim 11, wherein said first probe moiety, or said second probe moiety comprises coumarin.

26. The method of claim 11, wherein said first probe moiety, or said second probe moiety comprises 7-hydroxy coumarin.

27. The method of claim 11, wherein said first probe moiety, or said second probe moiety comprises rhodamine.

28. The method of claim 27, wherein said first probe moiety, or said second probe moiety comprises rhodamine B.

29. The method of claim 11, wherein said first probe moiety, or said second probe moiety comprises fluorescein.

30. The method of claim 29, wherein said first probe moiety, or said second probe moiety comprises fluorescein-5-isothiocyanate.

31. The method of claim 11, wherein said first probe moiety, or said second probe moiety comprises a lanthanide complex.

* * * * *